United States Patent
Hariton et al.

(10) Patent No.: US 10,426,614 B2
(45) Date of Patent: Oct. 1, 2019

(54) MINIMALLY-INVASIVE DELIVERY SYSTEMS

(71) Applicant: CARDIOVALVE LTD., Or Yehuda (IL)

(72) Inventors: Ilia Hariton, Zichron Yaakov (IL); Boaz Harari, Ganey Tikva (IL); Maxim Karalnik, Karmiel (IL); Michael Albitov, Kiryat Ono (IL); Meni Iamberger, Kfar Saba (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 15/899,858

(22) Filed: Feb. 20, 2018

(65) Prior Publication Data

US 2018/0185148 A1    Jul. 5, 2018

Related U.S. Application Data

(63) Continuation of application No. 15/886,517, filed on Feb. 1, 2018, now Pat. No. 10,154,903, which is a continuation of application No. PCT/IL2017/050849, filed on Aug. 1, 2017.

(30) Foreign Application Priority Data

Aug. 1, 2016 (GB) .................................. 1613219.3

(51) Int. Cl.
*A61F 2/24* (2006.01)
*A61F 2/966* (2013.01)
*A61F 2/958* (2013.01)

(52) U.S. Cl.
CPC .......... *A61F 2/2433* (2013.01); *A61F 2/2436* (2013.01); *A61F 2/966* (2013.01); *A61F 2002/9583* (2013.01)

(58) Field of Classification Search
None
See application file for complete search history.

(56) References Cited

U.S. PATENT DOCUMENTS 5,314,473 A    5/1994 Godin
5,954,766 A    9/1999 Zadno-Azizi et al.
(Continued)

FOREIGN PATENT DOCUMENTS

EP    1768630 B1    4/2007
WO    98/43557 A1   10/1998
(Continued)

OTHER PUBLICATIONS

Invitation to pay additional fees, dated Jan. 2, 2018; PCT/IL2017/050849.
(Continued)

*Primary Examiner* — Shaun L David
(74) *Attorney, Agent, or Firm* — Ladas & Parry LLP

(57) ABSTRACT

A tool is configured for transluminal delivery of an implant. The tool has a proximal part and a distal part, and comprises a shaft, a nosepiece, a sheath, and a balloon. The nosepiece is fixed to the shaft, and is arranged with respect to the implant such that the implant extends proximally away from the nosepiece and over the shaft. The sheath houses the implant. The balloon is disposed at the distal part of the tool, and is in fluid communication with the proximal part of the tool. When maximally inflated, the balloon has (i) a widest part that has an inflated diameter that is less than the diameter of the sheath or at most 10 percent greater than the diameter of the sheath, and (ii) a tapered portion that tapers longitudinally away from the widest part and from the nosepiece.

18 Claims, 16 Drawing Sheets

(56) References Cited

U.S. PATENT DOCUMENTS

| | | |
|---|---|---|
| 6,193,686 B1 | 2/2001 | Estrada et al. |
| 6,264,700 B1 | 7/2001 | Kilcoyne et al. |
| 6,402,780 B2 | 6/2002 | Williamson, IV et al. |
| 6,458,153 B1 | 10/2002 | Bailey et al. |
| 6,478,807 B1 | 11/2002 | Foreman et al. |
| 6,491,711 B1 | 12/2002 | Durcan |
| 6,669,724 B2 | 12/2003 | Park et al. |
| 6,764,518 B2 | 7/2004 | Godin |
| 6,884,257 B1 | 4/2005 | Cox |
| 6,951,571 B1 | 10/2005 | Srivastava et al. |
| 7,316,716 B2 | 1/2008 | Egan |
| 7,442,204 B2 | 10/2008 | Schwammenthal et al. |
| 7,776,080 B2 | 8/2010 | Bei et al. |
| 7,837,645 B2 | 11/2010 | Bessler et al. |
| 8,029,557 B2 | 10/2011 | Sobrino-Serrano et al. |
| 8,038,720 B2 | 10/2011 | Wallace et al. |
| D652,927 S | 1/2012 | Braido et al. |
| D653,341 S | 1/2012 | Braido et al. |
| D660,433 S | 5/2012 | Braido et al. |
| D660,967 S | 5/2012 | Braido et al. |
| 8,474,460 B2 | 7/2013 | Barrett et al. |
| 8,500,821 B2 | 8/2013 | Sobrino-Serrano et al. |
| 8,579,964 B2 | 11/2013 | Lane et al. |
| 8,591,460 B2 | 11/2013 | Wilson et al. |
| 8,673,020 B2 | 3/2014 | Sobrino-Serrano et al. |
| 8,784,481 B2 | 7/2014 | Alkhatib et al. |
| 8,852,272 B2 | 10/2014 | Gross et al. |
| 8,876,800 B2 | 11/2014 | Behan |
| 8,906,083 B2 | 12/2014 | Obermiller et al. |
| 8,986,375 B2 | 3/2015 | Garde et al. |
| 8,998,982 B2 | 4/2015 | Richter et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,155,619 B2 | 10/2015 | Liu et al. |
| 9,248,014 B2 | 2/2016 | Lane et al. |
| D755,384 S | 5/2016 | Pesce et al. |
| 9,326,876 B2 | 5/2016 | Acosta et al. |
| 9,387,078 B2 | 7/2016 | Gross et al. |
| 9,427,303 B2 | 8/2016 | Liddy et al. |
| 9,474,638 B2 | 10/2016 | Robinson et al. |
| 9,498,314 B2 | 11/2016 | Behan |
| 9,510,947 B2 | 12/2016 | Straubinger et al. |
| 9,566,152 B2 | 2/2017 | Schweich, Jr. et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,817 B2 | 9/2017 | Roeder |
| 2001/0002445 A1 | 5/2001 | Vesely |
| 2002/0177894 A1 | 11/2002 | Acosta et al. |
| 2003/0060875 A1 | 3/2003 | Wittens |
| 2003/0069635 A1 | 4/2003 | Cartledge et al. |
| 2004/0133267 A1 | 7/2004 | Lane |
| 2004/0210304 A1 | 10/2004 | Seguin et al. |
| 2005/0027305 A1 | 2/2005 | Shiu et al. |
| 2005/0137690 A1 | 6/2005 | Salahieh et al. |
| 2005/0149160 A1 | 7/2005 | McFerran |
| 2005/0240200 A1 | 10/2005 | Bergheim |
| 2006/0004439 A1 | 1/2006 | Spenser et al. |
| 2006/0020327 A1 | 1/2006 | Lashinski et al. |
| 2006/0041189 A1 | 2/2006 | Vancaillie |
| 2006/0111773 A1 | 5/2006 | Rittgers et al. |
| 2006/0116750 A1* | 6/2006 | Hebert .................. A61F 2/95 623/1.11 |
| 2006/0155357 A1 | 7/2006 | Melsheimer |
| 2006/0241745 A1 | 10/2006 | Solem |
| 2006/0259137 A1 | 11/2006 | Artof et al. |
| 2007/0027528 A1 | 2/2007 | Agnew |
| 2007/0027549 A1 | 2/2007 | Godin |
| 2007/0078510 A1 | 4/2007 | Ryan |
| 2008/0071361 A1 | 3/2008 | Tuval et al. |
| 2008/0082159 A1 | 4/2008 | Tseng et al. |
| 2008/0091261 A1 | 4/2008 | Long et al. |
| 2008/0132989 A1* | 6/2008 | Snow .................. A61F 2/95 623/1.12 |
| 2008/0269879 A1 | 10/2008 | Sathe et al. |
| 2009/0005863 A1 | 1/2009 | Goetz et al. |
| 2009/0036966 A1 | 2/2009 | O'Connor et al. |
| 2009/0088836 A1 | 4/2009 | Bishop et al. |
| 2009/0099554 A1 | 4/2009 | Forster et al. |
| 2009/0240320 A1 | 9/2009 | Tuval et al. |
| 2009/0264859 A1* | 10/2009 | Mas .................. A61F 2/95 604/509 |
| 2009/0276040 A1 | 11/2009 | Rowe et al. |
| 2009/0281619 A1* | 11/2009 | Le .................. A61M 25/01 623/2.11 |
| 2010/0069852 A1 | 3/2010 | Kelley |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2011/0137397 A1 | 6/2011 | Chau et al. |
| 2011/0144742 A1* | 6/2011 | Madrid .................. A61F 2/2433 623/2.11 |
| 2011/0208283 A1 | 8/2011 | Rust |
| 2011/0213459 A1* | 9/2011 | Garrison .................. A61F 2/013 623/2.11 |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0282439 A1 | 11/2011 | Thill et al. |
| 2011/0288632 A1 | 11/2011 | White |
| 2011/0295354 A1 | 12/2011 | Bueche et al. |
| 2011/0313515 A1 | 12/2011 | Quadri et al. |
| 2011/0319989 A1 | 12/2011 | Lane et al. |
| 2012/0053676 A1 | 3/2012 | Ku et al. |
| 2012/0059337 A1 | 3/2012 | Eilat |
| 2012/0078237 A1* | 3/2012 | Wang .................. A61F 2/2436 606/1 |
| 2012/0078353 A1 | 3/2012 | Quadri et al. |
| 2012/0101571 A1 | 4/2012 | Thambar et al. |
| 2012/0300063 A1 | 11/2012 | Majkrzak et al. |
| 2013/0018458 A1 | 1/2013 | Yohanan et al. |
| 2013/0035759 A1 | 2/2013 | Gross et al. |
| 2013/0079872 A1* | 3/2013 | Gallagher .................. A61F 2/2436 623/2.11 |
| 2013/0190861 A1 | 7/2013 | Chau et al. |
| 2013/0231735 A1 | 9/2013 | Deem et al. |
| 2013/0289711 A1 | 10/2013 | Liddy et al. |
| 2013/0304200 A1 | 11/2013 | McLean et al. |
| 2014/0121749 A1 | 5/2014 | Roeder |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0277418 A1 | 9/2014 | Miller |
| 2014/0336744 A1 | 11/2014 | Tani et al. |
| 2014/0343670 A1 | 11/2014 | Bakis et al. |
| 2015/0018944 A1 | 1/2015 | O'Connell et al. |
| 2015/0119970 A1 | 4/2015 | Nakayama et al. |
| 2015/0148894 A1 | 5/2015 | Damm et al. |
| 2015/0173896 A1 | 6/2015 | Richter et al. |
| 2015/0238313 A1 | 8/2015 | Spence et al. |
| 2015/0245934 A1 | 9/2015 | Lombardi et al. |
| 2015/0272730 A1 | 10/2015 | Melnick et al. |
| 2015/0282964 A1 | 10/2015 | Beard et al. |
| 2015/0327994 A1 | 11/2015 | Morriss et al. |
| 2015/0335429 A1 | 11/2015 | Morriss et al. |
| 2015/0342736 A1 | 12/2015 | Rabito et al. |
| 2015/0351904 A1 | 12/2015 | Cooper et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0220367 A1 | 8/2016 | Barrett |
| 2016/0228247 A1 | 8/2016 | Maimon et al. |
| 2016/0270911 A1 | 9/2016 | Ganesan et al. |
| 2016/0317301 A1 | 11/2016 | Quadri et al. |

| | | | |
|---|---|---|---|
| 2016/0331526 | A1 | 11/2016 | Schweich, Jr. et al. |
| 2016/0331527 | A1 | 11/2016 | Vidlund et al. |
| 2017/0042678 | A1 | 2/2017 | Ganesan et al. |
| 2017/0056166 | A1 | 3/2017 | Ratz et al. |
| 2017/0056171 | A1 | 3/2017 | Cooper et al. |
| 2017/0128205 | A1 | 5/2017 | Tamir et al. |
| 2017/0196688 | A1 | 7/2017 | Christianson et al. |
| 2017/0196692 | A1 | 7/2017 | Kirk et al. |
| 2017/0209264 | A1 | 7/2017 | Chau et al. |
| 2017/0216026 | A1 | 8/2017 | Quill et al. |
| 2017/0231759 | A1 | 8/2017 | Geist et al. |
| 2017/0231760 | A1 | 8/2017 | Lane et al. |
| 2018/0049873 | A1 | 2/2018 | Manash et al. |
| 2018/0055628 | A1 | 3/2018 | Patel et al. |
| 2018/0055630 | A1 | 3/2018 | Patel et al. |
| 2018/0153689 | A1 | 6/2018 | Maimon et al. |
| 2018/0177594 | A1 | 6/2018 | Patel et al. |
| 2018/0296341 | A1 | 10/2018 | Noe et al. |

FOREIGN PATENT DOCUMENTS

| | | |
|---|---|---|
| WO | 2005/107650 A2 | 11/2005 |
| WO | 2006/007401 A2 | 1/2006 |
| WO | 2007/059252 A1 | 5/2007 |
| WO | 2008/031103 A2 | 3/2008 |
| WO | 2008/070797 A2 | 6/2008 |
| WO | 2009/091509 A1 | 7/2009 |
| WO | 2010/037141 A1 | 4/2010 |
| WO | 2010/057262 A1 | 5/2010 |
| WO | 2010/121076 A2 | 10/2010 |
| WO | 2011/025972 A2 | 3/2011 |
| WO | 2012/024428 A2 | 2/2012 |
| WO | 2012/036740 A2 | 3/2012 |
| WO | 2014/194178 A1 | 12/2014 |
| WO | 2017/223486 A1 | 12/2017 |
| WO | 2018/025260 A1 | 2/2018 |
| WO | 2018/108837 A1 | 6/2018 |
| WO | 2018/112429 A1 | 6/2018 |
| WO | 2018/118717 A1 | 6/2018 |
| WO | 2018/131042 A1 | 7/2018 |
| WO | 2018/131043 A1 | 7/2018 |

OTHER PUBLICATIONS

UK Office Action dated Feb. 8, 2017; UK Appln. No. 1613219.3.
USPTO NFOA dated Oct. 23, 2017 in connection with U.S. Appl. No. 14/763,004.
USPTO FOA dated Jan. 17, 2018 in connection with U.S. Appl. No. 14/763,004.
USPTO NFOA dated Feb. 7, 2018 in connection with U.S. Appl. No. 15/197,069.
USPTO NFOA dated Dec. 7, 2017 in connection with U.S. Appl. 15/213,791.
Interview summary dated Feb. 8, 2018 in connection with U.S. Appl. No. 15/213,791.
USPTO NFOA dated Jan. 5, 2018 in connection with U.S. Appl. No. 15/541,783
USPTO NFOA dated Feb. 2, 2018 in connection with U.S. Appl. No. 15/329,920.
An Office Action dated Jun. 6, 2018, which issued during the prosecution of UK Patent Application No. 1720803.4.
An Office Action dated Jun. 18, 2018, which issued during the prosecution of UK Patent Application No. 1800399.6.
International Search Report and Written Opinion dated Jun. 20, 2018 PCT/IL2018/050024.
USPTO AA dated Apr. 2, 2018 in connection with U.S. Appl. No. 14/763,004.
USPTO NFOA dated Jun. 28, 2018 in connection with U.S. Appl. No. 29/635,658.
USPTO NFOA dated Jun. 28, 2018 in connection with U.S. Appl. No. 29/635,661.
USPTO NFOA dated Jul. 26, 2018 in connection with U.S. Appl. No. 15/872,501.
NSPTO NFOA dated Aug. 9, 2018 in connection with U.S. Appl. No. 15/902,403.
USPTO NFOA dated Apr. 20, 2018 in connection with U.S. Appl. No. 15/886,517.
USPTO RR dated May 4, 2018 in connection with U.S. Appl. No. 15/872,501.
USPTO NOA dated Apr. 20, 2018 in connection with U.S. Appl. No. 15/878,206.
Extended European Search Report dated Sep. 26, 2018; Appln. No. 18186784.7.
The First Chinese Office Action dated Nov. 5, 2018; Appln. No. 201680008328.5.
Invitation to pay additional fees dated Oct. 11, 2018; PCT/IL2018/050725.
USPTO NFOA dated Dec. 4, 2018 in connection with U.S. Appl. No. 16/045,059.
USPTO NOA dated Sep. 25, 2018 in connection with U.S. Appl. No. 15/188,507.

* cited by examiner

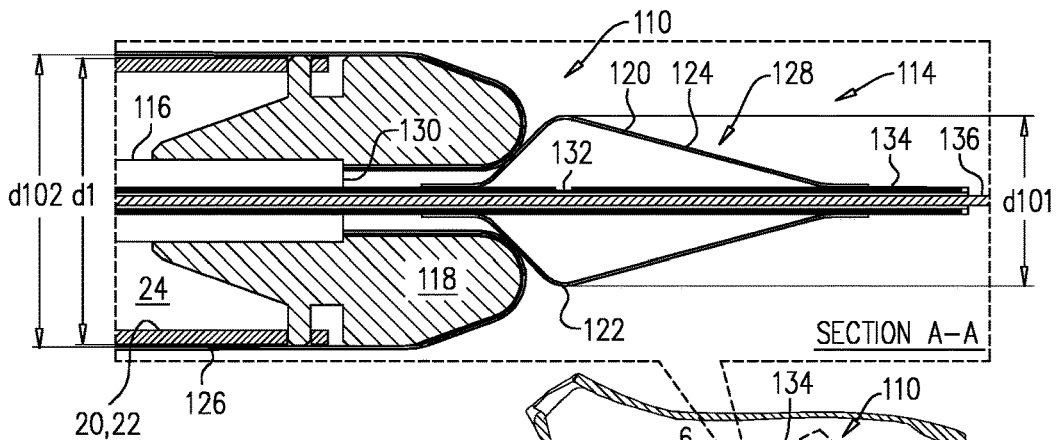
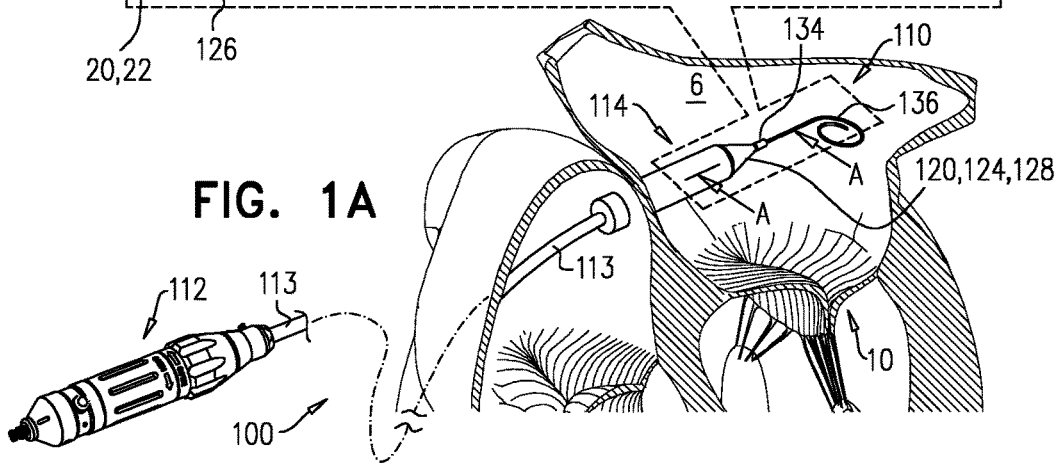
FIG. 1A
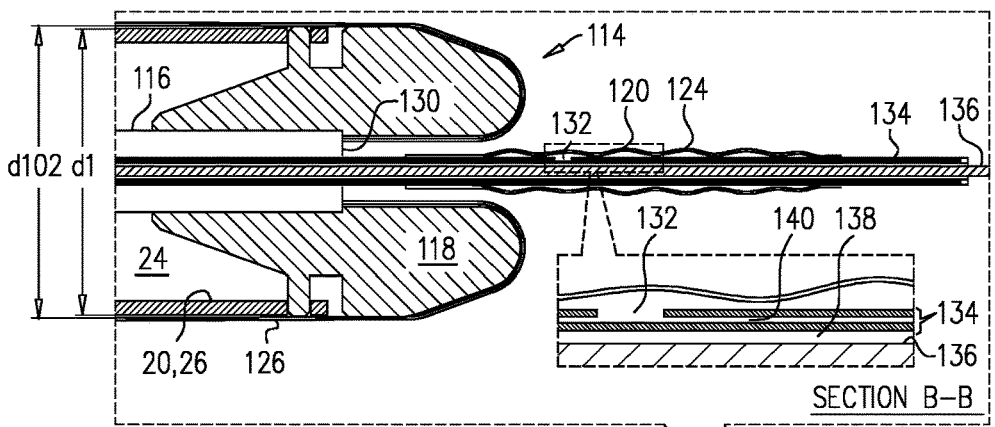
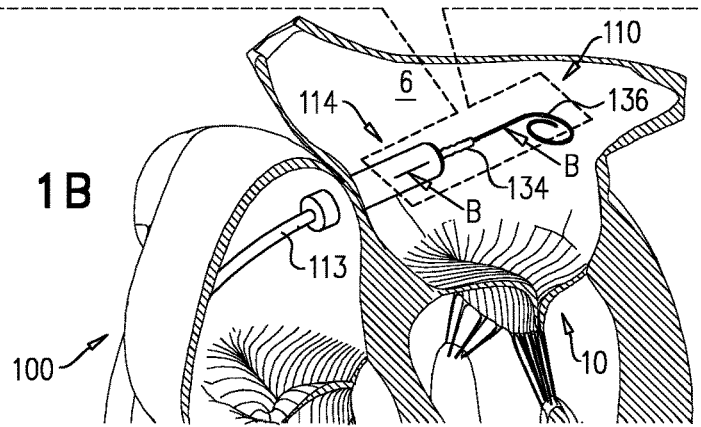
FIG. 1B

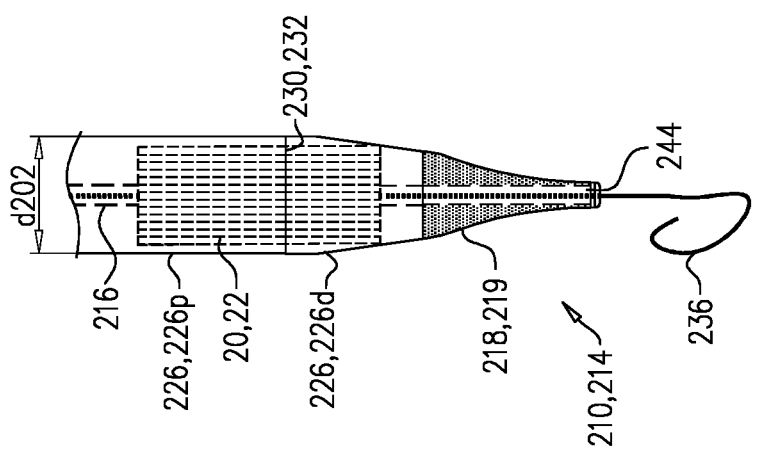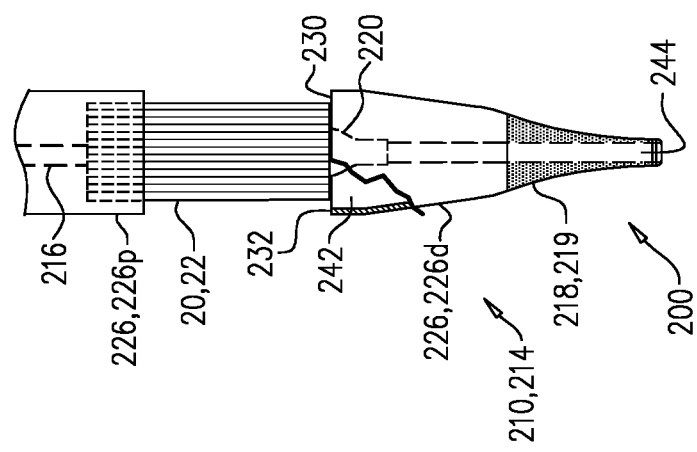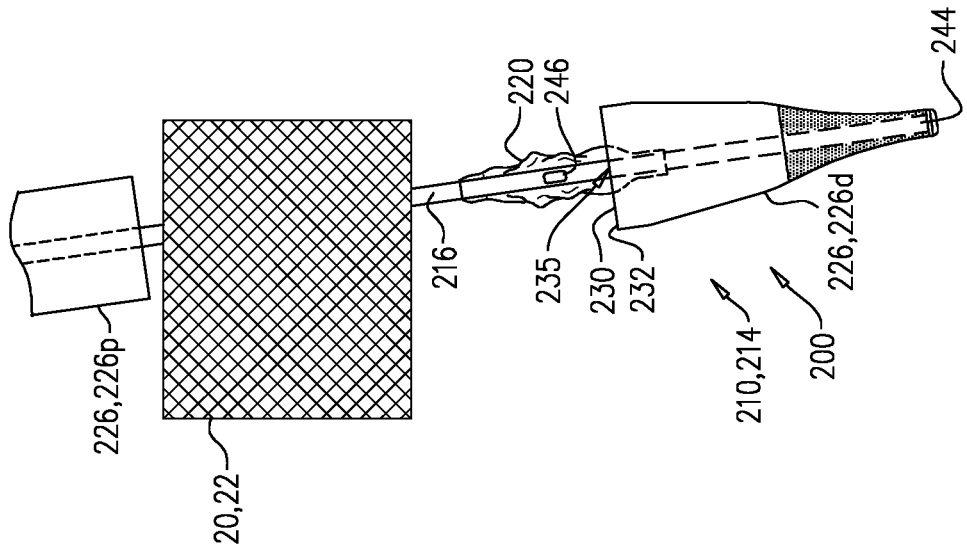

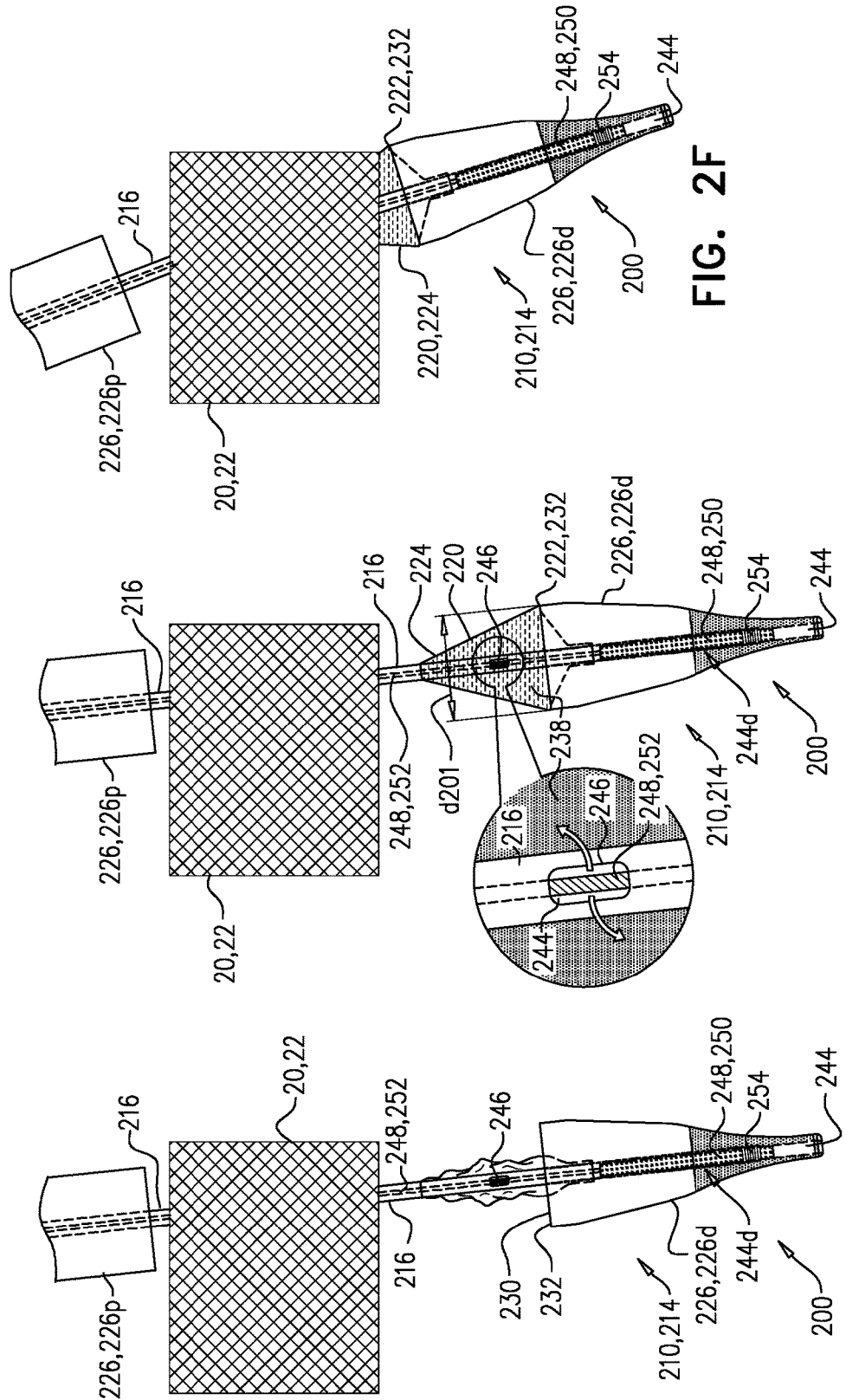

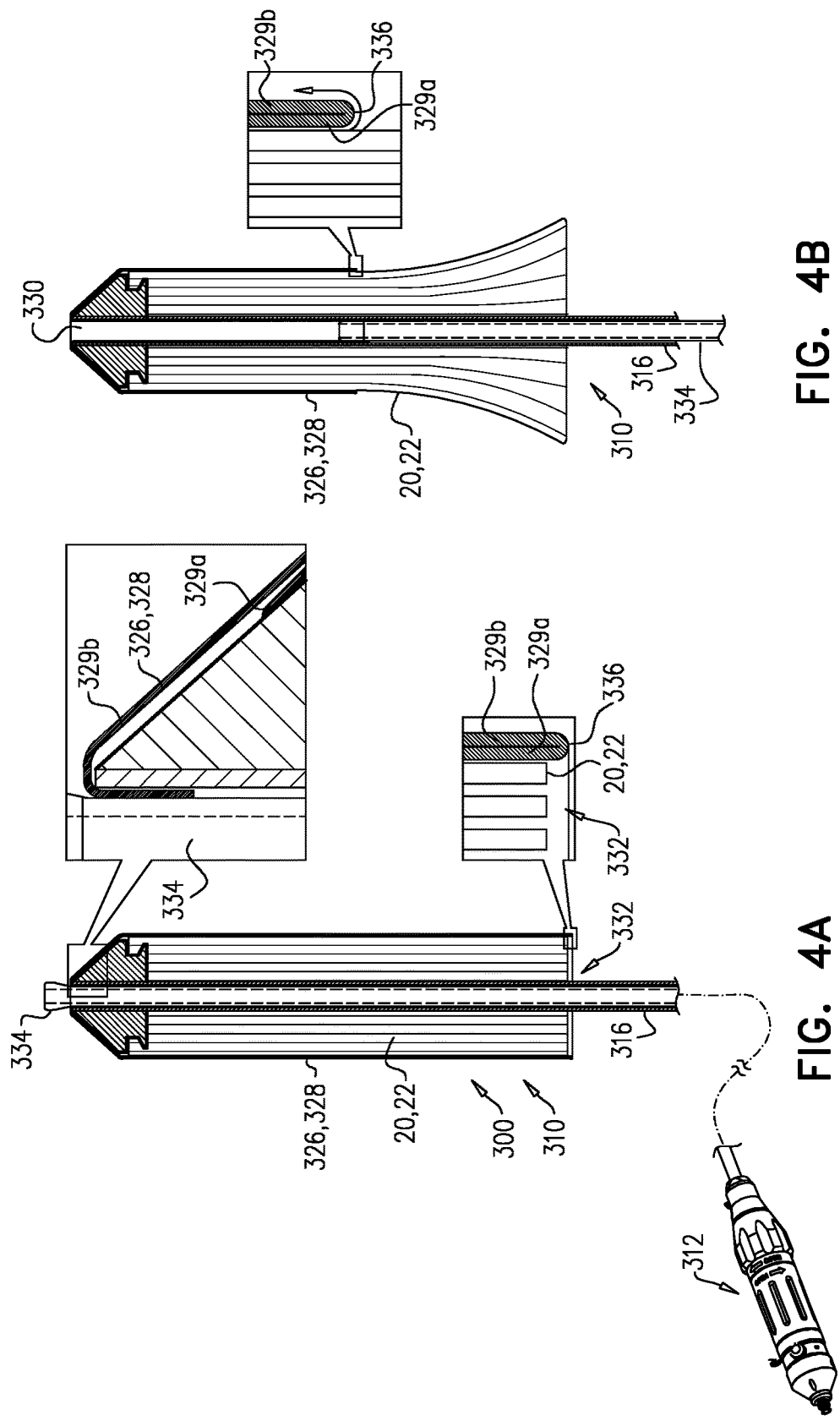

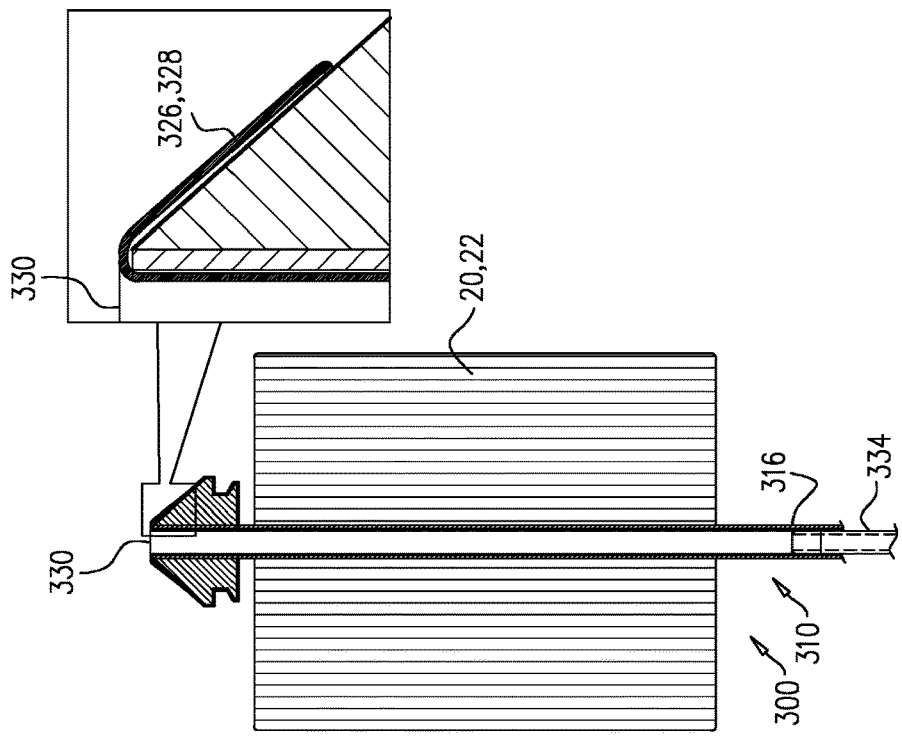
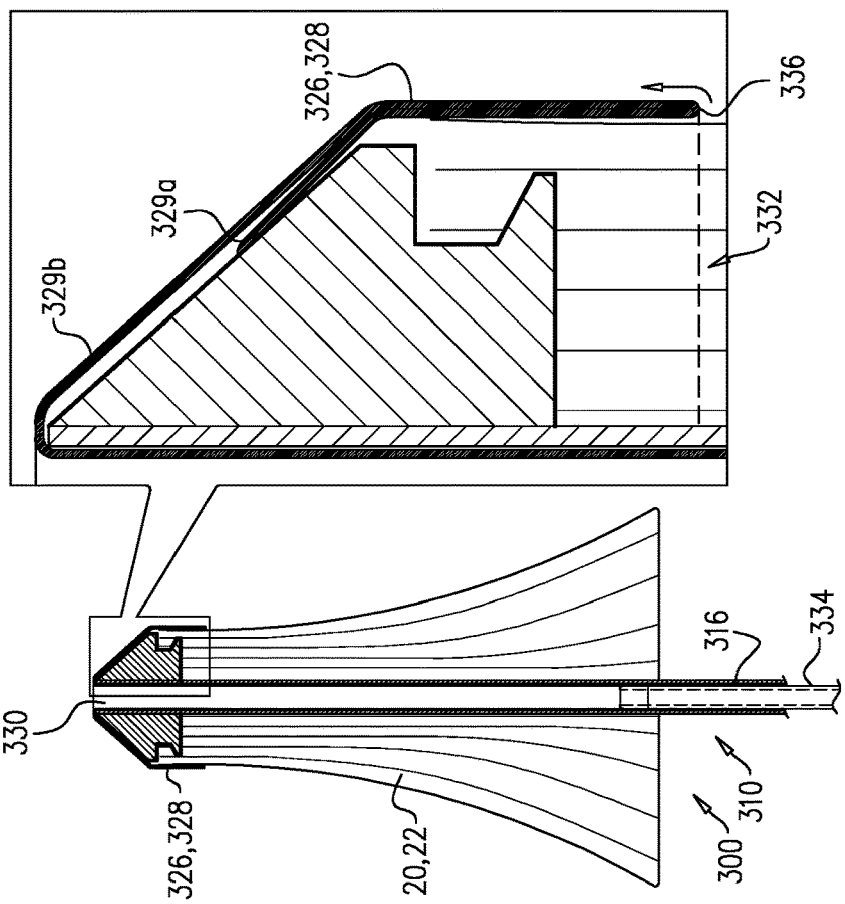

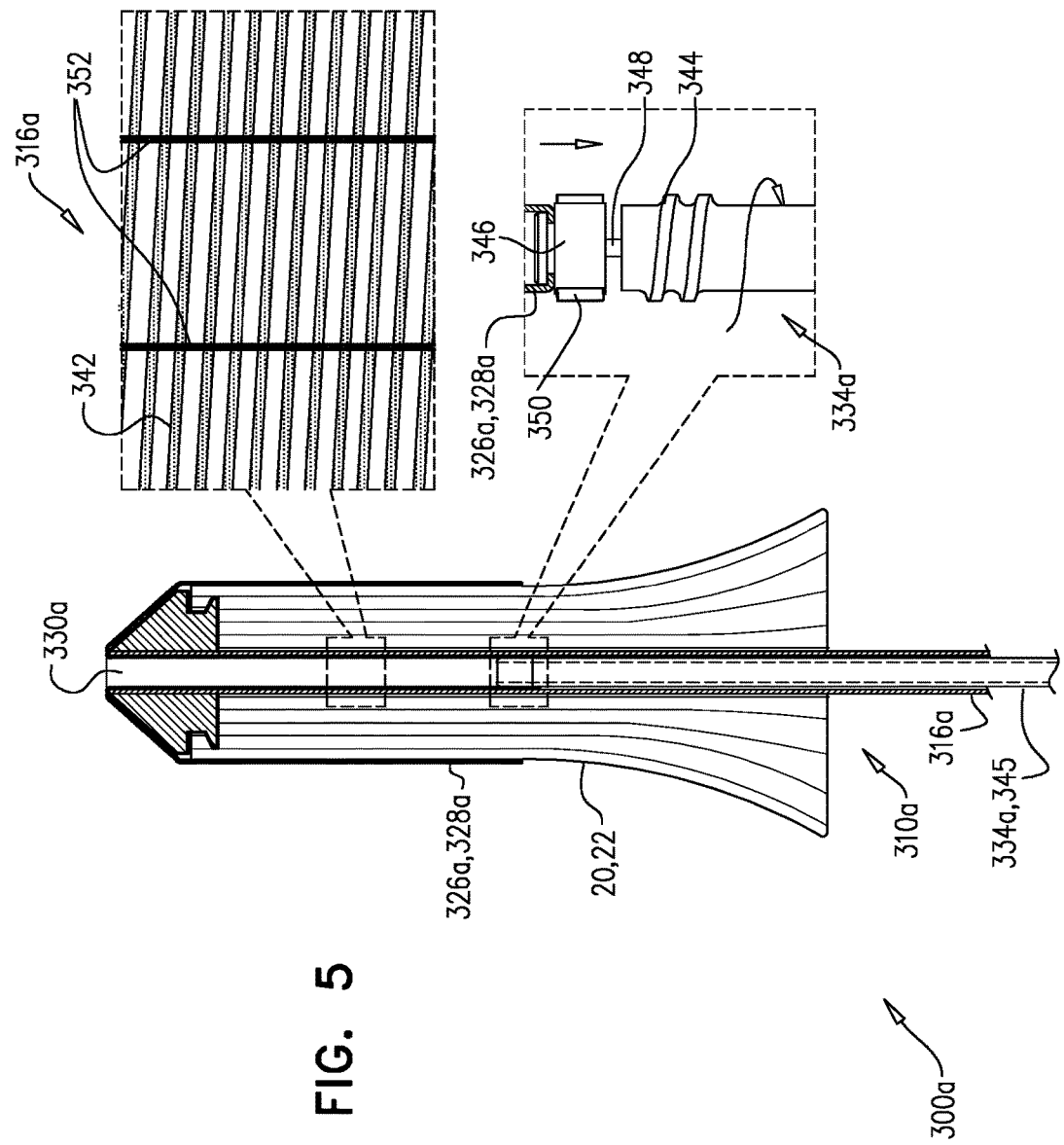

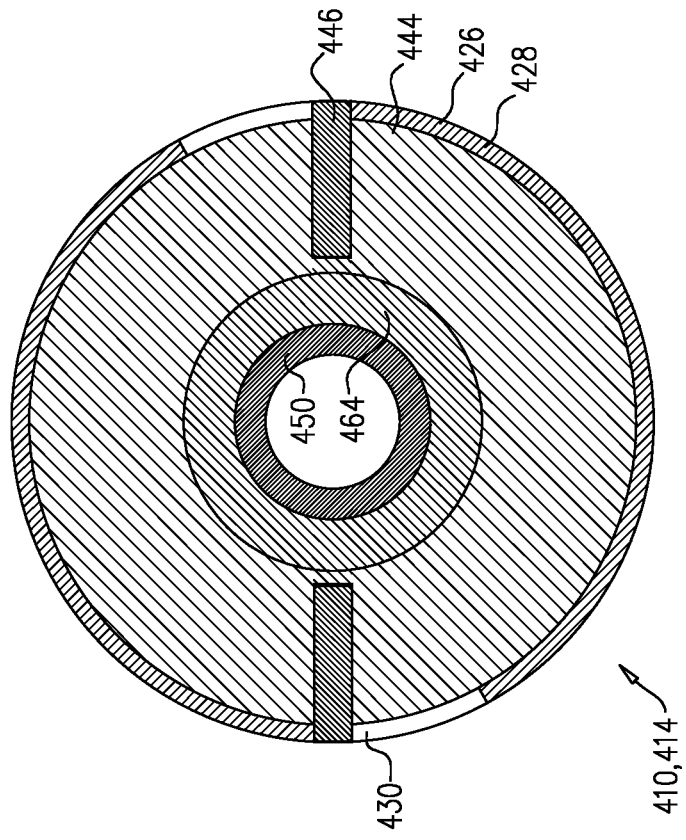
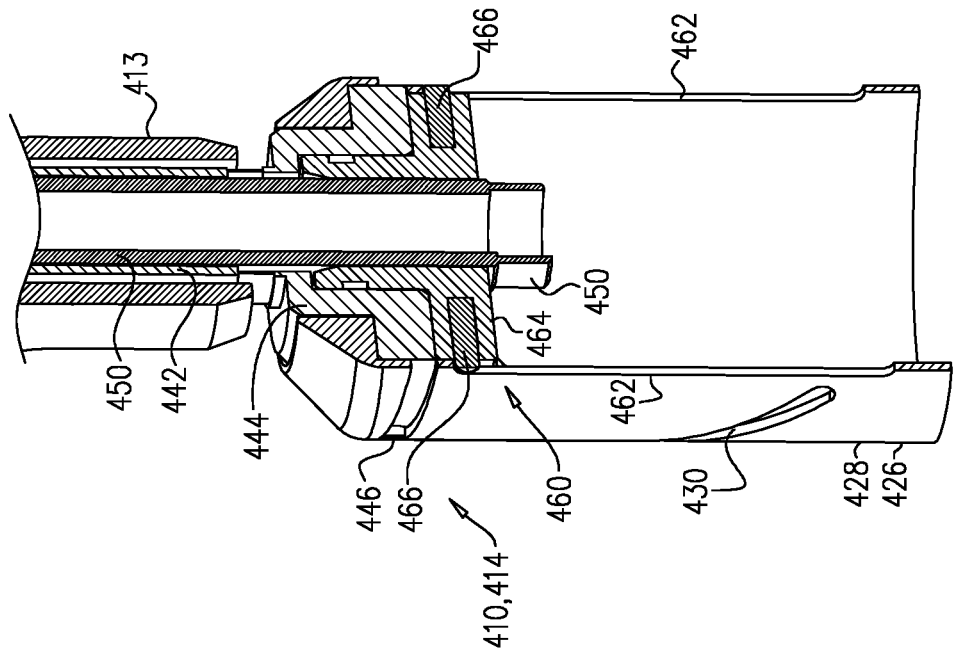

MINIMALLY-INVASIVE DELIVERY SYSTEMS

CROSS-REFERENCES TO RELATED APPLICATIONS

The present application is a Continuation of U.S. patent application Ser. No. 15/886,517 to Albitov et al., filed Feb. 1, 2018, and entitled "Minimally-invasive delivery systems," which is a Continuation of PCT application IL2017/050849 to Hariton et al., filed Aug. 1, 2017, and entitled "Minimally-invasive delivery systems," which claims priority from UK patent application GB1613219.3, filed Aug. 1, 2016, and entitled "Minimally-invasive delivery systems," all of which are incorporated herein by reference.

FIELD OF THE INVENTION

Some applications of the present invention relate in general to valve replacement. More specifically, some applications of the present invention relate to prosthetic cardiac valves and techniques for implantation thereof.

BACKGROUND

Dilation of the annulus of a heart valve, such as that caused by ischemic heart disease, prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

Systems are described, each of which comprises a delivery tool for an implant, the delivery tool comprising a balloon at a distal portion of the tool. The balloon facilitates movement of the distal portion of the tool past potential anatomical and/or implanted obstacles, e.g., by providing a tapered surface. One described balloon serves as a nosecone of the delivery tool, facilitating distal movement of the distal portion of the tool through the vasculature. Another described balloon serves as a reverse nosecone that facilitates proximal movement of the distal portion of the tool through the implanted implant.

Also described is a sheath for retaining the implant on the distal portion of a delivery tool, and a system for unsheathing the implant.

Also described is a delivery tool that comprises a housing that defines a generally-helical track, and a controller that comprises an actuator. At least part of an implant is housed by the housing. Rotation of the actuator draws the housing proximally with respect to the implant by sliding an engaging element of the actuator along the track. This proximal movement of the housing deploys the implant from within the housing.

The technologies described may be used separately on different delivery tools, or in various combinations on a single delivery tool.

There is therefore provided, in accordance with an application of the present invention, apparatus, for use with an implant, the apparatus including a tool, the tool including:
a housing, at a distal part of the tool, the housing:
including a tubular wall that circumscribes a longitudinal axis of the distal part of the tool,
dimensioned to house at least part of the implant, and
defining a track that follows a generally-helical path around the longitudinal axis; and
a controller, including:
a rod that extends from a proximal part of the tool to the housing; and
an actuator, fixedly coupled to the rod, including an engaging element that engages the track, and rotatable with respect to the housing, the controller and the housing mechanically cooperating such that rotation of the actuator with respect to the housing slides the housing longitudinally with respect to the actuator.

In an application:
the housing is a proximal housing, and the part of the implant is a first part of the implant;
the proximal housing is configured to house the first part of the implant, and has a distal opening for deployment of the first part of the implant therethrough; and
the tool further includes a distal housing that is configured to house a second part of the implant, and has a proximal opening for deployment of the second part of the implant therethrough, the proximal opening of the distal housing facing the distal opening of the proximal housing.

In an application, the housing is dimensioned to house at least the part of the implant such that at least the part of the implant is coincident along the longitudinal axis with at least part of the track.

In an application, the housing is dimensioned to house at least the part of the implant such that the generally-helical path around the longitudinal axis is also around at least the part of the implant, and at least part of the track follows the generally-helical path around the longitudinal axis and at least the part of the implant.

In an application:
the tool further includes a catheter,
the rod extends through the catheter,
the controller and the housing mechanically cooperate such that rotation of the actuator with respect to the housing slides the housing proximally along and over part of the catheter.

In an application, the controller and the housing mechanically cooperate such that rotation of the actuator in a first direction with respect to the housing slides the housing proximally with respect to the actuator, and rotation of the actuator in a second, opposite direction with respect to the housing slides the housing distally with respect to the actuator.

In an application, the track is a first track, and the housing further includes a second track that follows a generally-linear path parallel to the longitudinal axis.

In an application, the track is a channel, and the engaging element is a spur that engages the track by protruding into the channel.

In an application, the track is a rail, and the engaging element is a notch that engages the track by receiving the rail.

In an application:
a first portion of the generally-helical path has a first pitch,
a second portion of the generally-helical path has a second pitch, the second portion being distal to the first portion, and
the second pitch being greater than the first pitch, and
the track follows the generally-helical path that has the first portion that has the first pitch and the second portion that has the second pitch.

In an application:
the generally-helical path has a pitch that is progressively greater at progressively distal portions of the generally-helical path, and the track follows the generally-helical path that has the pitch that is progressively greater at progressively distal portions of the generally-helical path.

In an application, the apparatus further includes the implant.

In an application, the apparatus further includes a shaft to which the implant is fixable, the shaft being slidably coupled to the housing, and extending proximally from the housing.

In an application:
the track is a first track,
the engaging element is a first engaging element,
the housing further includes a second track that follows a generally-linear path parallel to the longitudinal axis,
the tool further includes a second engaging element, fixedly coupled to the shaft, the second engaging element engaging the second track such that the shaft is rotationally fixed with respect to the housing.

In an application, the controller and the housing mechanically cooperate such that rotation of the actuator with respect to the housing slides the second track longitudinally with respect to the second engaging element.

In an application, the apparatus further includes the implant, fixedly coupled to the shaft, at least the part of the implant housed by the housing.

In an application, the rod is coaxial with the shaft.

In an application, the shaft is disposed within the rod.

In an application, the actuator defines a hole through which the shaft extends.

In an application, the shaft is rotationally fixed with respect to the housing.

In an application, at least part of the shaft is disposed within the housing.

There is further provided, in accordance with an application of the present invention, a method, including:
transluminally advancing, into a heart of a subject, a distal part of a tool, the distal part of the tool including a housing, the housing:
including a tubular wall that circumscribes a longitudinal axis of the distal part of the tool,
housing at least part of an implant, and
defining a track that follows a generally-helical path around the longitudinal axis; and
retracting the housing from at least the part of the implant by rotating a rod that is fixedly coupled to an actuator that includes an engaging element that is engaged with the track, such that the actuator rotates with respect to the housing and causes the housing to slide longitudinally with respect to the actuator.

There is further provided, in accordance with an application of the present invention, apparatus, including:
an implant; and
a tool, configured for transluminal delivery of the implant, the tool having a proximal part and a distal part, and including:
a shaft that extends longitudinally from the proximal part of the tool to the distal part of the tool;
a nosepiece, fixed to the shaft, and arranged with respect to the implant such that the implant extends proximally away from the nosepiece and over the shaft;
a sheath, configured to house the implant during transluminal delivery, and having a diameter that is dimensioned for transluminal delivery; and
a balloon, disposed at the distal part of the tool, and in fluid communication with the proximal part of the tool, and the balloon has:
a maximally-inflated state in which the balloon (i) has a widest part that has an inflated diameter that is less than the diameter of the sheath or at most 10 percent greater than the diameter of the sheath, and (ii) has a tapered portion that tapers longitudinally away from the widest part and from the nosepiece, and
a deflated state in which the widest part has a deflated diameter that is smaller than the inflated diameter.

In an application, the nosepiece is fixed to the distal end of the shaft.

In an application, the tapered portion tapers distally away from the widest part and from the nosepiece.

In an application, the tapered portion tapers proximally away from the widest part and from the nosepiece.

In an application, the apparatus has a delivery state in which the implant, the sheath, and the balloon are transluminally advanceable into a subject, and in which:
the implant is in a compressed state, and is housed by the sheath, and
the balloon is in its maximally-inflated state.

In an application, the apparatus has a delivery state in which the implant, the sheath, and the balloon are transluminally advanceable into a subject, and in which:
the implant is in a compressed state, and is housed by the sheath, and
the balloon is in its deflated state.

In an application, the balloon is slidably coupled to the shaft at least in the deflated state of the balloon.

In an application:
the implant (i) is constrainable, by a constraining force, in a compressed state in which the implant has a compressed diameter, and (ii) has an expanded state into which the implant automatically transitions upon removal of the constraining force, and in which the implant has an expanded diameter, and
the maximally-inflated diameter of the balloon is smaller than the expanded diameter of the implant.

In an application:
the implant is shaped to define a lumen therethrough,
the nosepiece is arranged with respect to the implant such that the implant extends proximally over the shaft with the shaft within the lumen of the implant,
the implant has an expanded state, and assumes the expanded state upon implantation of the implant, and
the nosepiece is dimensioned to be withdrawable proximally through the lumen while the implant is in its expanded state.

In an application, the implant is self-expanding to the expanded state.

In an application, the implant has a compressed state for transluminal delivery, and the nosepiece is not dimensioned to be withdrawable proximally through the lumen while the implant is in its compressed state.

There is further provided, in accordance with an application of the present invention, apparatus, including:
an implant:
constrainable, by a constraining force, in a compressed state in which the implant has a compressed diameter,
having an expanded state into which the implant automatically transitions upon removal of the constraining force, and in which the implant has an expanded diameter; and
a tool, configured for transluminal delivery of the implant, the tool including:
a shaft that extends longitudinally from a proximal part of the tool;
a nosepiece, fixed to the shaft, and arranged with respect to the implant such that the implant extends proximally away from the nosepiece and over the shaft; and a balloon, in fluid communication with the proximal part of the tool, and the balloon has:

a maximally-inflated state in which the balloon (i) has a widest part that has an inflated diameter that is smaller than the expanded diameter, and (ii) has a tapered portion that tapers longitudinally away from the widest part and from the nosepiece, and a deflated state in which the widest part has a deflated diameter that is smaller than the inflated diameter.

In an application, the nosepiece is fixed to the distal end of the shaft.

In an application, the tapered portion tapers distally away from the widest part and from the nosepiece.

In an application, the tapered portion tapers proximally away from the widest part and from the nosepiece.

In an application, the balloon is slidably coupled to the shaft at least in the deflated state of the balloon.

In an application:

the implant (i) is constrainable, by a constraining force, in a compressed state in which the implant has a compressed diameter, and (ii) has an expanded state into which the implant automatically transitions upon removal of the constraining force, and in which the implant has an expanded diameter, and the maximally-inflated diameter of the balloon is smaller than the expanded diameter of the implant.

In an application:

the implant is shaped to define a lumen therethrough, the nosepiece is arranged with respect to the implant such that the implant extends proximally over the shaft with the shaft within the lumen of the implant, the implant has an expanded state, and assumes the expanded state upon implantation of the implant, and the nosepiece is dimensioned to be withdrawable proximally through the lumen while the implant is in its expanded state.

In an application, the implant is self-expanding to the expanded state.

In an application, the implant has a compressed state for transluminal delivery, and the nosepiece is not dimensioned to be withdrawable proximally through the lumen while the implant is in its compressed state.

In an application, the tool further includes a sheath that is configured to house the implant during transluminal delivery, and has a diameter that is dimensioned for transluminal delivery.

In an application, the apparatus has a delivery state in which the implant, the sheath, and the balloon are transluminally advanceable into a subject, and in which:

the implant is in a compressed state, and is housed by the sheath, and the balloon is in its maximally-inflated state.

In an application, the apparatus has a delivery state in which the implant, the sheath, and the balloon are transluminally advanceable into a subject, and in which:

the implant is in a compressed state, and is housed by the sheath, and the balloon is in its deflated state.

There is further provided, in accordance with an application of the present invention, apparatus, including:

an implant; and a tool, configured for transluminal delivery of the implant, the tool including:

a shaft that extends longitudinally from a proximal part of the;

a nosepiece, fixed to the shaft, and arranged with respect to the implant such that the implant extends proximally away from the nosepiece and over the shaft; and a balloon, inflatable from a proximal part of the tool, and coupled to the shaft such that when inflated the balloon has a tapered portion that tapers distally away from the nosepiece.

In an application, the nosepiece is fixed to the distal end of the shaft.

In an application:

the implant:

is constrainable, by a constraining force, in a compressed state in which the implant has a compressed diameter, and has an expanded state into which the implant automatically transitions upon removal of the constraining force, and in which the implant has an expanded diameter; and the balloon has:

a maximally-inflated state in which (i) the balloon has a widest part that has an inflated diameter that is smaller than the expanded diameter of the implant, and (ii) the tapered portion tapers distally away from the nosepiece and from the widest part, and a deflated state in which the widest part has a deflated diameter that is smaller than the inflated diameter.

In an application, the balloon is slidably coupled to the shaft at least in the deflated state of the balloon.

In an application:

the implant is shaped to define a lumen therethrough, the nosepiece is arranged with respect to the implant such that the implant extends proximally over the shaft with the shaft within the lumen of the implant, the implant has an expanded state, and assumes the expanded state upon implantation of the implant, and the nosepiece is dimensioned to be withdrawable proximally through the lumen while the implant is in its expanded state.

In an application, the implant is self-expanding to the expanded state.

In an application, the implant has a compressed state for transluminal delivery, and the nosepiece is not dimensioned to be withdrawable proximally through the lumen while the implant is in its compressed state.

In an application, the tool further includes a sheath that is configured to house the implant during transluminal delivery, and has a diameter that is dimensioned for transluminal delivery.

In an application, the apparatus has a delivery state in which the implant, the sheath, and the balloon are transluminally advanceable into a subject, and in which:

the implant is in a compressed state, and is housed by the sheath, and the balloon is in its maximally-inflated state.

In an application, the apparatus has a delivery state in which the implant, the sheath, and the balloon are transluminally advanceable into a subject, and in which:

the implant is in a compressed state, and is housed by the sheath, and the balloon is in its deflated state.

There is further provided, in accordance with an application of the present invention, apparatus, including:

an implant; and a tool, configured for transluminal delivery of the implant, the tool including:

a shaft that extends longitudinally from a proximal part of the tool to a distal end of the shaft, and has an opening at the distal end, the opening having an opening diameter, and the implant being reversibly coupled to the tool and disposed around the shaft; and a nosecone:
coupled to the shaft such that the nosecone has (i) a widest part that is disposed outside the opening, and has a diameter that is greater than the opening diameter, and (ii) a tapered portion that tapers distally away from the opening and the implant, and withdrawable through the opening into the shaft.

In an application, the nosecone is inflatable.

In an application, the tool further includes a sheath that is configured to house the implant during transluminal delivery, and has a diameter that is dimensioned for transluminal delivery.

There is further provided, in accordance with an application of the present invention, apparatus for use with an implant, the apparatus including a delivery tool, the delivery tool including:

a sheath that defines a cavity dimensioned to house at least a portion of the implant, and has a lip that defines a proximal opening via which the portion of the implant is removable from the cavity;

a shaft that:
extends longitudinally from a proximal part of the tool to the sheath, and
is coupled to the sheath such that shaft passes through the proximal opening, and the lip circumscribes a longitudinal site of the shaft; and a balloon disposed over the shaft at at least the longitudinal site, and inflation of the balloon obstructs the opening.

In an application, the balloon is positioned and dimensioned such that inflation of the balloon brings the balloon in contact with the lip.

In an application, the sheath has a diameter, and the balloon has a maximally-inflated state in which the balloon has a widest part that has an inflated diameter that is less than the diameter of the sheath or at most 10 percent greater than the diameter of the sheath.

In an application, the balloon has a maximally-inflated state in which the balloon has a tapered portion that tapers proximally away from the opening.

In an application:
the implant (i) is constrainable, by a constraining force, in a compressed state in which the implant has a compressed diameter, and (ii) has an expanded state into which the implant automatically transitions upon removal of the constraining force, and in which the implant has an expanded diameter, and
the balloon has a maximally-inflated state in which the balloon is smaller than the expanded diameter of the implant.

In an application, the balloon has a deflated state for delivery of the implant, and a maximally-inflated state, and inflation of the balloon to the maximally-inflated state obstructs at least 80 percent of the opening.

In an application, when the balloon is in the deflated state, the opening is at least 50 percent unobstructed by either the balloon or the shaft.

In an application, the apparatus has a delivery state in which the implant, the sheath, and the balloon are transluminally advanceable into a subject, and in which:
the implant is in a compressed state, and is housed by the sheath, and
the balloon is in its deflated state.

In an application, in the delivery state the implant is compressed around the balloon.

There is further provided, in accordance with an application of the present invention, apparatus, including:
an implant; and
a tool, configured for transluminal delivery of the implant, the tool including:
a shaft that extends longitudinally from a proximal part of the tool, and has an open distal end, the implant being reversibly coupled to the tool and disposed around a distal portion of the shaft;
a sheath that houses the implant, and has a diameter that is dimensioned for transluminal delivery; and
a control element, disposed within the shaft, movement of the control element within the shaft being controllable by the proximal part of the tool, and the control element being coupled to the sheath such that movement of the control element proximally within the shaft draws the sheath (i) distally off of the implant, and (ii) into the open distal end of the shaft.

In an application, the sheath includes a flexible sheet.

In an application, the sheet is doubled-over itself to define an inner wall of the sheath, and an outer wall of the sheath.

In an application, the sheet defines a proximal opening of the sheath at a transition zone between the inner wall and the outer wall, and the movement of the control element proximally within the shaft peels the sheath distally off of the implant by drawing the outer wall progressively into the open distal end of the shaft such that progressively proximal regions of the inner wall transition through the transition zone to become part of the outer wall, and the proximal opening of the sheath moves distally along the implant.

In an application:
the control element includes a shank that extends through the shaft, and a coupling rotatably coupled to a distal end of the shank;
the control element is coupled to the sheath by the coupling being coupled to the sheath; and
the shank defines an outer screw thread;
the shaft defines an inner screw thread that is complementary to the outer screw thread; and
the control element and the shaft are configured such that rotation of the shank with respect to the sheath provides the movement of the control element proximally within the shaft by (i) screwing the shank through the shaft, but (ii) slides the coupling linearly through the shaft.

In an application, the shaft defines an inner linear groove that extends longitudinally along the shaft, and the coupling defines a fin that extends outward and into the inner groove, disposition of the fin within the groove inhibiting rotation of the coupling with respect to the shaft but allowing longitudinal sliding of the coupling through the shaft.

In an application, the inner screw thread and the inner linear groove are defined by the same longitudinal region of the shaft.

In an application, the inner screw thread and the inner linear groove transect each other.

There is further provided, in accordance with an application of the present invention, a method, for use with a subject, the method including:
transluminally advancing, into a subject, an implant housed within a cavity defined by a sheath of a tool, the tool including a balloon;
subsequently, intracorporeally removing the implant from the cavity via a proximal opening of the cavity;
subsequently, obstructing the proximal opening by inflating the balloon; and
subsequently, while the balloon is inflated, withdrawing the balloon and the sheath via a lumen of the implant.

The present invention will be more fully understood from the following detailed description of applications thereof, taken together with the drawings, in which:

BRIEF DESCRIPTION OF THE DRAWINGS

FIGS. 1A-F are schematic illustrations of a system comprising an implant and a tool configured for transluminal delivery of the implant, in accordance with some applications of the invention;

FIGS. 2A-F and 3 are schematic illustrations of another system comprising the implant and a tool configured for transluminal delivery of the implant, in accordance with some applications of the invention; and FIGS. 4A-D are schematic illustrations of another system comprising the implant and a tool configured for transluminal delivery of the implant, in accordance with some applications of the invention;

FIG. 5 is a schematic illustration of another system comprising the implant and a tool configured for transluminal delivery of the implant, in accordance with some applications of the invention;

FIGS. 6A-C and 7A-C are schematic illustrations of a tool for use with an implant, in accordance with some applications of the invention.

DETAILED DESCRIPTION OF EMBODIMENTS

Figure 1C:
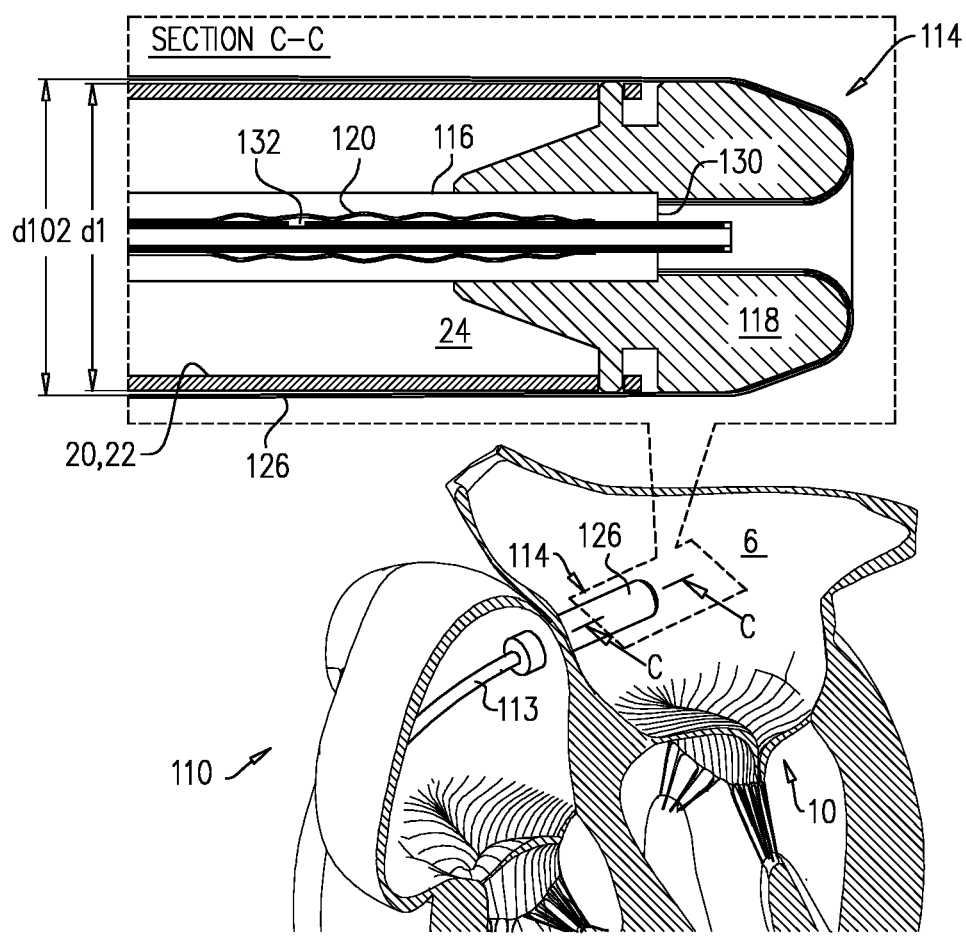

Reference is made to FIGS. 1A-F and to FIGS. 2A-F and 3, which are schematic illustrations of a system 100 and a system 200, respectively, in accordance with some applications of the invention. Each of systems 100 and 200 comprises an implant 20 and a tool 110 (system 100) or 210 (system 200), the tool configured for transluminal delivery of the implant. For some applications, and as shown, implant 20 is a prosthetic heart valve (e.g., a prosthetic mitral valve). However, implant 20 may alternatively be a different type of implant. Typically, implant 20 comprises a tubular portion 22 that defines a lumen 24 through the implant (at least in an implanted and/or expanded state of the implant). Implant 20 may further comprise additional features such as anchoring elements (not shown). For applications in which implant 20 is a prosthetic valve, the implant further comprises a valve member, such as one or more prosthetic leaflets, disposed within lumen 24.

Each of tools 110 and 210 is configured for transluminal delivery of implant 20, and has a proximal part (e.g., a proximal part 112 of tool 110; the proximal part of tool 210 may be similar, mutatis mutandis) and a distal part 114 (tool 110) or 214 (tool 210). The proximal part is typically an extracorporeal part (e.g., comprising a handle, port(s) and/or controllers), and the distal part is transluminally advanceable into a subject (e.g., to the heart of the subject). Each of tools 110 and 210 further comprises:

(1) a shaft 116 (tool 110) or 216 (tool 210) that extends longitudinally from the proximal part of the tool to the distal part of the tool;

(2) a nosepiece 118 (tool 110) or 218 (tool 210), fixed to the shaft (e.g., to the distal end of the shaft), and arranged with respect to the implant such that the implant extends proximally away from the nosepiece and over the shaft (e.g., with the shaft disposed within a lumen defined by the implant); and (3) a balloon 120 (tool 110) or 220 (tool 210) disposed at the distal part of the tool, and in fluid communication with the proximal part of the tool (e.g., inflatable from the proximal part of the tool).

Each of balloons 120 and 220 has (i) a maximally-inflated state in which the balloon has a widest part (122 or 222, respectively) that has an inflated diameter (d101 or d201, respectively), and a tapered portion (124 or 224, respectively) that tapers longitudinally away from the widest part and from the nosepiece, and (ii) a deflated state in which the widest part has a deflated diameter that is smaller than the inflated diameter. The maximally-inflated state of balloon 120 is shown, for example, in FIG. 1A, and the maximally-inflated state of balloon 220 is shown, for example, in FIGS. 2E-F.

Balloons 120 and 220 are not configured (e.g., dimensioned or arranged with respect to implant 20) for expanding implant 20 at the implant site. Rather, the tapered portion facilities smooth intracorporeal movement of the tool. For example, and as described hereinbelow, balloon 120 facilitates movement of tool 110 distally through the vasculature of the subject, and balloon 220 facilitates withdrawal of tool 210 from implant 20.

Typically, each of tools 110 and 210 further comprises a sheath (126 or 226, respectively), configured to house the implant (e.g., at least part of the implant) during transluminal delivery, and having a diameter (d102 or d202, respectively) that is dimensioned for transluminal delivery.

Typically, implant 20 is an expandable implant, having a compressed diameter d1 (FIG. 1A) for transluminal delivery, and an expanded diameter d2 (FIG. 1E) for functioning at the implant site. Typically, the compressed and expanded diameters refer to those of tubular portion 22 (rather than those of any additional features such as an anchoring element). For example, implant 20 (e.g., tubular portion 22) may be self-expanding (e.g., comprising a shape-memory material such as Nitinol), such that it (i) is constrainable in a compressed state by a constraining force, and (ii) has an expanded state into which it automatically transitions upon removal of the constraining force. For such applications, the constraining force is typically provided by a sheath, such as sheath 126 of tool 110 or housing 426 of tool 410, and removal of the constraining force occurs when the implant becomes deployed from the sheath.

For some applications, the maximally-inflated diameter of the balloon is smaller than expanded diameter d2 of implant 20 (e.g., the expanded diameter of tubular portion 22). For example, the inflated diameter of the balloon may be less than 90 percent (e.g., less than 80 percent, e.g., less than 70 percent, e.g., less than 60 percent, e.g., less than 50 percent, e.g., less than 40 percent, e.g., less than 30 percent, e.g., less than 20 percent, e.g., less than 10 percent) of the expanded diameter of the implant. It is to be noted that balloons 120 and 220 thus differ from balloons used for expanding plastically-expandable implants, inter alia, in this regard because such implant-expanding balloons necessarily expand to a diameter that is significantly greater than that of the compressed diameter of the implant, in order to expand the implant from its delivery state to its expanded state at the implantation site. For some applications, the inflated diameter of the balloon is less than the diameter of the sheath or is at most 10 percent greater than the diameter of the sheath. For example, the inflated diameter of the balloon may be 20-110 percent, (such as 20-100 percent, or 30-110 percent) the diameter of the sheath, e.g., 30-110 percent (such as 30-100 percent or 40-110 percent), e.g., 40-110 percent (such as 40-100 percent or 50-110 percent), e.g., 50-110 percent (such as 50-100 percent or 60-110 percent), e.g., 60-110 percent (such as 60-100 percent or 70-110 percent), e.g., 70-110 percent (such as 70-100 percent or 80-110 percent), e.g., 80-110 percent (such as 80-100 percent or 90-110 percent), e.g., 90-110 percent (such as 90-100 percent or 100-110 percent). The inflated diameter of the balloon may be less than 90 percent (e.g., less than 80 percent, e.g., less than 70 percent, e.g., less than 60 percent, e.g., less than 50 percent) the diameter of the sheath. It is to be noted that balloons 120 and 220 thus differ from balloons used for expanding plastically-expandable implants, inter alia, in this regard because such implant-expanding balloons necessarily expand to a diameter that is significantly greater than that of the sheath, in order to expand the implant from its delivery state within the sheath, to its expanded state at the implantation site.

Reference is now made to FIGS. 1A-F. System 100 comprises implant 20, and tool 110. Tool 110 is configured for transluminal delivery of the implant, and comprises shaft 116, nosepiece 118, and balloon 120. In its maximally-inflated state (FIG. 1A), tapered portion 124 of balloon 120 tapers distally away from nosepiece 118 (and typically from implant 20). Balloon 120 (or tapered portion 124 thereof) therefore defines a nosecone 128 of tool 110, the nosecone facilitating transluminal advancement of the tool, such as transfemoral advancement into the aorta and/or transseptal advancement into the left atrium 6.

It is to be noted that the term "maximally-inflated state" (including in the specification and the claims) means the state in which the balloon has the inherent maximum volume provided by the dimensions into which the material from which it is made is formed (e.g., the maximum inflation before plastic deformation and/or rupture occurs).

FIG. 1A thus shows system 100 in a delivery state thereof, in which the implant, the sheath, and the balloon are transluminally advanceable into a subject. In the delivery state of system 100, (i) implant 20 is in a compressed state, and is housed by the sheath 126, and (ii) balloon 120 is in its maximally-inflated state. For some applications, diameter 101 of balloon 120 in its maximally-inflated state is 1-9 mm (e.g., 3-6 mm).

Nosecones are known in the art for advancement of devices (e.g., tools, catheters, etc.) through the vasculature. However, the presence of such nosecones adds to the length of the device. For some applications, it is important to reduce the length of the device, or particular parts thereof. For example, a delivery tool for transseptal (e.g., transfemoral) implantation of a prosthetic mitral valve (e.g., tool 110) turns sharply downward after passing through the interatrial septum 7 (e.g., at the fossa ovalis) in order (i) to pass between the leaflets of the native mitral valve 10, and (ii) to be angled (or to angle the implant therewithin) appropriately for implantation (e.g., perpendicular to the native mitral valve). The required sharpness of this turn is at least partly dictated by (i) the height d4 of atrium 6 from mitral valve 10 (e.g., the mitral annulus) to the ceiling of the atrium, (ii) the height d5 between the mitral valve and the entry point 5 of tool 110 through septum 7 (e.g., the fossa ovalis), and/or (iii) the distance across atrium 6, perpendicular to heights d4 and d5, between septum 7 and the target site—typically the center of mitral valve 10.

Because nosecone 128 is defined by balloon 120, the length of tool 110 (e.g., distal part 114 thereof) is reducible by at least deflating balloon 120. Deflation is typically performed after passage through septum 7 and before the turning of distal part 114 toward native mitral valve 10, thereby facilitating this turning.

Typically, when in its deflated state, balloon 120 is withdrawable into an opening 130 at the distal end of shaft 116, whereas inflated diameter d101 is greater than the diameter of opening 130. Therefore, nosecone 128 defined by balloon 120 is:

(1) coupled to shaft 116 such that the nosecone has (i) a widest part 122 that is disposed outside opening 130, and has a diameter d101 that is greater than the opening diameter, and (ii) a tapered portion 124 that tapers distally away from the opening and implant 20, and (2) withdrawable (e.g., slidable) through opening 130 into shaft 116.

Balloon 120 is typically fixed to a control rod 134 that is slidable within shaft 116. Control rod 134 is typically slidable over a guidewire 136 (e.g., the rod has a first lumen 138 within which the guidewire is disposed). Balloon 120 is typically also inflatable and deflatable via control rod 134, which may have a secondary lumen 140 (e.g., parallel with or coaxially surrounding the lumen 138) that has one or more openings 132 into balloon 120. Therefore, at least in its deflated state, balloon 120 is slidably coupled to shaft 116 (e.g., via rod 134).

Figure 1D:
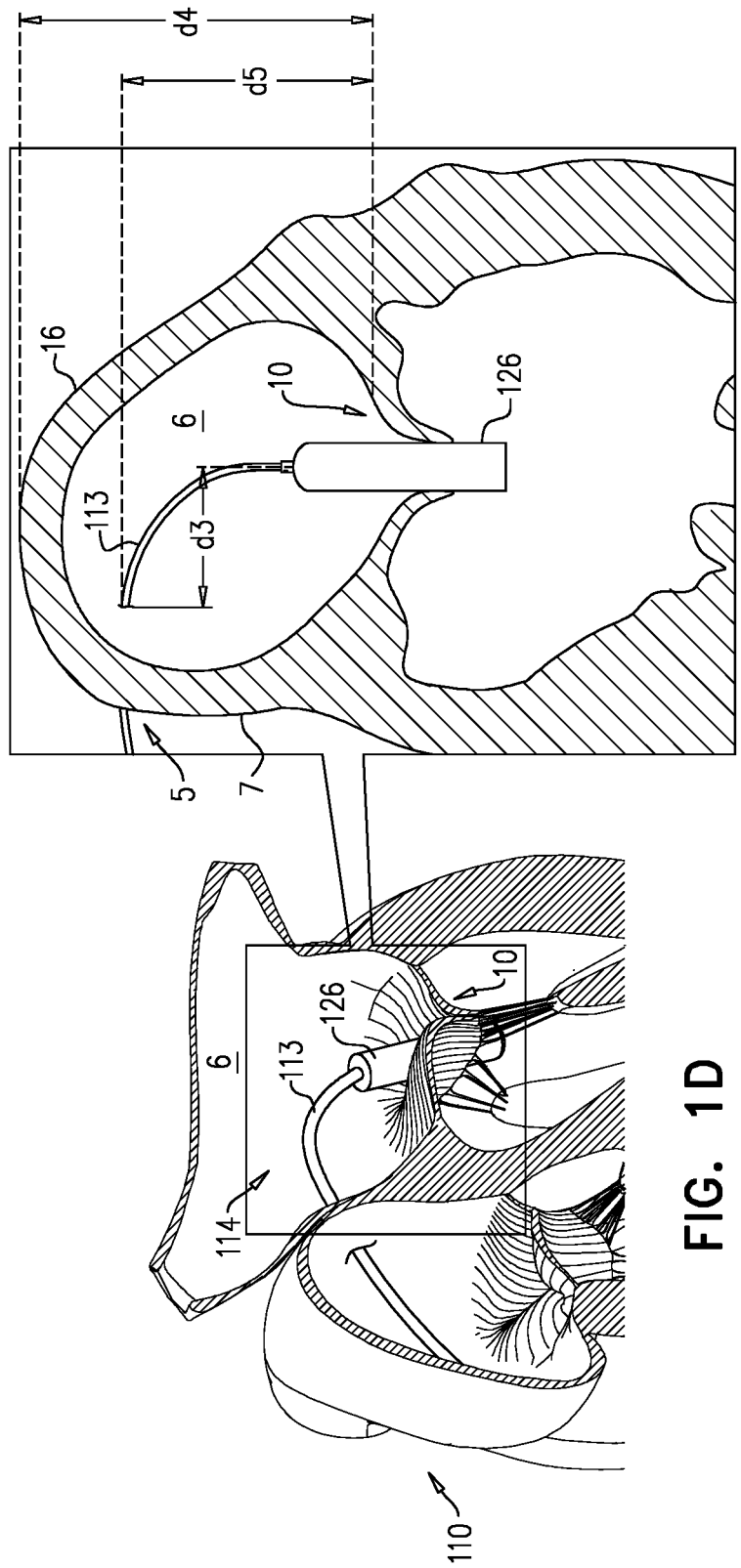

FIG. 1B shows balloon 120 in its deflated state, and FIG. 1C shows the balloon having been subsequently withdrawn into shaft 116, thereby reducing the overall length of tool 110. Subsequently, distal part 114 of tool 110 is steered toward native mitral valve 10, and between the leaflets thereof (FIG. 1D). As described hereinabove, the prior reduction in the length of tool 110 reduces a likelihood of tissue of the heart interfering with this steering. Typically, this steering is achieved using a steerable mid-portion 113 (e.g., a steerable catheter) that extends from proximal part 112 to distal part 114, and through which shaft 116 extends.

Figure 1E:
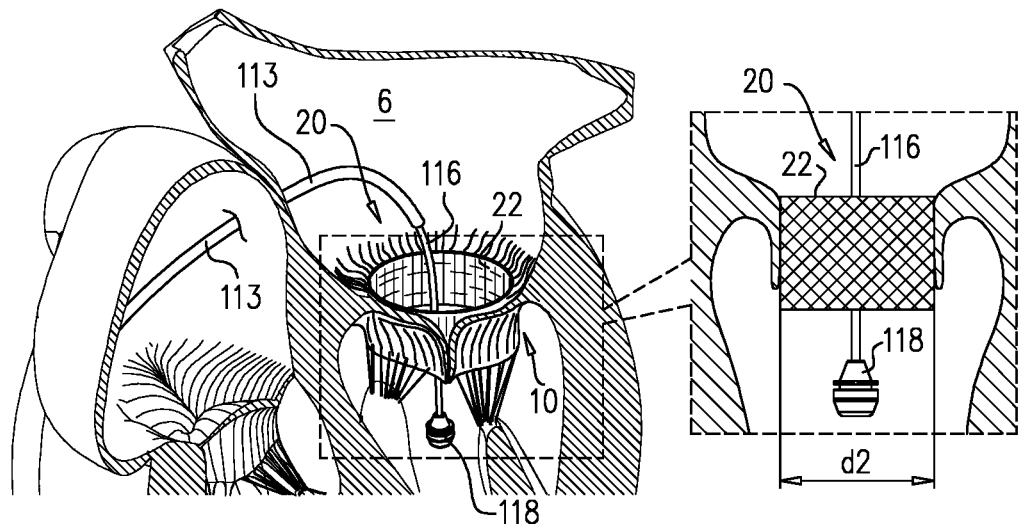
Figure 1F:
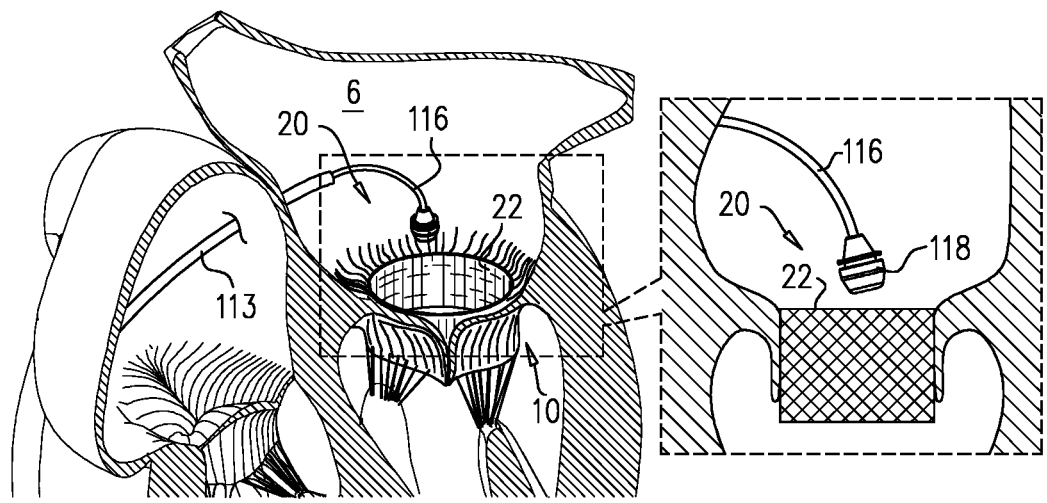

Once distal part 114 of the tool 110 is positioned at the implantation site (e.g., at native mitral valve 10), implant 20 is deployed from sheath 126. FIG. 1E shows implant 20 having expanded, upon deployment, into its expanded state. Typically, implant 20 is a self-expanding implant, e.g., comprising Nitinol or another elastic material. Typically, despite this expansion, shaft 116 remains disposed through a lumen defined by the implant until it, and nosepiece 118, are withdrawn proximally through the lumen (FIG. 1F). For some applications, nosepiece 118 is not dimensioned to be withdrawable proximally through the lumen of implant 20 while the implant is in its compressed state. For example, implant 20 may be fixed to nosepiece 118 while in its compressed state, such that the nosepiece serves as an implant controller. For example, while nosepiece 118 is in one position with respect to sheath 126 it may maintain implant 20 within the sheath, and deployment of the implant may be executed by relative movement between the nosepiece and the sheath (e.g., controlled from the proximal part of tool 110).

Sheath 126 is not shown in FIGS. 1E-F, reflecting that, for some embodiments, sheath 126 is a flexible sheath that is drawn into shaft 116 during deployment of implant 20 (e.g., as described for sheath 326 with reference to FIGS. 4A-D, mutatis mutandis). However, it is to be noted that for some applications, sheath 126 is rigid (e.g., is a capsule) and is withdrawn while remaining disposed over part of shaft 116. (For such applications, sheath 126 would be visible in FIGS. 1E-F.)

There is therefore provided, a method, comprising: (1) transluminally advancing, into a subject, an implant housed within a cavity defined by a sheath of a tool, the tool including a balloon; (2) subsequently, intracorporeally removing the implant from the cavity via a proximal opening of the cavity; (3) subsequently, obstructing the proximal opening by inflating the balloon; and (4) subsequently, while the balloon is inflated, withdrawing the balloon and the sheath via a lumen of the implant.

Reference is now made to FIGS. 2A-F, and 3. System 200 comprises implant 20, and tool 210. Tool 210 is configured for transluminal delivery of the implant, and comprises shaft 216, nosepiece 218, and balloon 220. As described in more detail hereinbelow, in its maximally-inflated state (FIGS. 2E-F), tapered portion 224 of balloon 220 tapers proximally away from nosepiece 218.

FIG. 2A shows system 200 in a delivery state thereof, in which implant 20, sheath 226, and balloon 220 are transluminally advanceable into a subject, toward a delivery site (e.g., mitral valve 10). In the delivery state of system 200, (i) implant 20 is in a compressed state, and is housed by the sheath 226 (which typically constrains the implant in the compressed state), and (ii) balloon 220 is in its deflated state.

Sheath 226 defines a cavity 242 that is dimensioned to house at least a portion of implant 20, and has a lip 232 that defines a proximal opening 230 via which the housed portion of the implant is removable from the cavity. For some applications, sheath 226 comprises a distal piece 226d and a proximal piece 226p that face each other and house respective portions of implant 20, and the distal piece defines cavity 242 and proximal opening 230. (Sheath 226 may alternatively comprise only one piece, shaped generally like distal piece 226d.)

Shaft 216 extends longitudinally from the proximal part of the tool to distal part 214, at which sheath 226 and nosepiece 218 are disposed. Shaft 216 is coupled to the sheath such that shaft passes through proximal opening 230, and lip 232 circumscribes a longitudinal site 235 of the shaft. Typically, balloon 220 is disposed over the shaft at at least longitudinal site 235.

Shaft 216 extends through the lumen defined by implant 20, and is fixed to nosepiece 218, which is disposed distally to the implant. Typically, nosepiece 218 is fixed to sheath 226 (e.g., distal piece 226d thereof). For some applications, and as shown, sheath 226 (e.g., distal piece 226d thereof) is fixed to shaft 216 via nosepiece 218 (i.e., by being connected to the nosepiece, which itself is connected to the sheath). Typically, nosepiece 218 is fixed to the distal end of shaft 216. Nosepiece 218 serves as a nosecone 219; the advantages of a nosecone are described hereinabove. Typically, nosepiece 218 is not dimensioned to be withdrawable proximally through the lumen of implant 20 while the implant is in its compressed state.

Tool 210 is typically advanced to the implantation site over a guidewire 236. For example, shaft 216, sheath 226, and/or nosepiece 218 are shaped to define a lumen 244 through which guidewire 236 is slidable.

Once at the implantation site, the housed portion of implant 20 is removed from cavity 242 by moving distal piece 226d distally with respect to the implant (FIG. 2B). In addition, proximal piece 226p may be moved proximally with respect to the implant. Implant 20 is deployed by sufficiently (e.g., fully) exposing it from sheath 226. For applications in which implant 20 is self-expanding, the implant expands automatically after the constraining force provided by sheath 226 has been removed by sufficiently exposing the implant from the sheath.

FIG. 2C shows system 200 after implant 20 has been deployed from sheath 226. Nosepiece 218, distal piece 226d of sheath 226, and at least most (e.g., all) of balloon 220 are disposed distally to implant 20. For delivery tools that house an implant in a sheath that has a proximal opening (e.g., a two-piece sheath such as sheath 226, or a sheath that has only one piece shaped generally like distal piece 226d), withdrawal of the sheath after implantation of the implant is typically performed by withdrawing the sheath through the lumen of the implant. For example, in the case of a prosthetic valve, the sheath is typically withdrawn through the prosthetic valve, passing between its prosthetic leaflets. A risk exists that, should the distal part of the implantation tool be imperfectly aligned with the implanted implant, the lip (that defines the proximal opening through which the implant was previously withdrawn) may engage (e.g., catch onto) the implant, making withdrawal difficult and/or dislodging the implant. Balloon 220 reduces this risk.

Either before (as shown) or after implantation of implant 20, guidewire 236 is removed from lumen 244. For some applications, lumen 244 is in fluid communication with balloon 220, and the balloon is inflated via this lumen. For some such applications, this fluid communication is provided by a port 246 defined by shaft 216, and balloon 220 is inflated by delivering a fluid 238 (e.g., saline) via shaft 216, e.g., via the lumen 244 in which guidewire 236 was previously disposed. Because lumen 244 is open at a distal end, in order to provide fluid pressure for inflating balloon 220, a control rod 248 that is slidable within shaft 216 is slid into lumen 244 prior to inflation. Control rod 248 comprises a distal plug 250 that fits snugly within at least a distal region 244d of lumen 244 (distal to port 246), such that when the plug is introduced, it seals against the walls of lumen 244 (or at least distal region 244d thereof). For example, plug 250 may have an outer diameter that is at least 50 (e.g., at least 70, e.g., at least 90, such as at least 95) percent of the inner diameter of lumen 244. For some applications, and as shown, distal region 248d is defined by nosepiece 218 (e.g., nosecone 219). For some applications, and as shown, plug 250 defines an external screw thread 254, and is screwed into distal region 248d. For example, nosepiece 218 may comprise a flexible material such as silicone into which screw thread 254 may cut. (Alternatively, distal region 248d may be lined with such a material.) The flexible material may advantageously increase atraumatic properties of nosecone 219.

Control rod 248 further comprises a flexible proximal portion 252, which has a diameter that is less than 90 percent (e.g., 20-60 percent) of the inner diameter of lumen 244. Control rod 248 is dimensioned such that, while distal plug 250 is disposed at distal region 248d of lumen 244, proximal portion 252 extends distally through lumen 244 at least until port 246. Fluid introduced into lumen 244 at the proximal part of tool 210 flows along the lumen, alongside portion 252, and out of port 246, thereby inflating balloon 220 (FIG. 2E). Plug 250 inhibits the fluid from escaping at distal part 214 of tool 210.

It is to be noted that the scope of the invention includes other techniques for inflating balloon 220. For example, for some applications, shaft 216 may have a secondary lumen that opens into balloon 220, e.g., as described for lumen 140 of control rod 134 of system 100, mutatis mutandis.

FIG. 2E shows balloon 220 in its maximally-inflated state. Inflation of balloon 220 obstructs opening 230. For some applications, and as shown, inflation of balloon 220 obstructs at least 80 percent (e.g., at least 90 percent) of opening 230, e.g., obstructs opening 230 completely (e.g., sealing up the opening). For example, widest part 222 may have an inflated diameter that is equal to, or slightly (e.g., 1-10 percent) greater than the diameter of opening 230, and balloon 220 comes into contact with (e.g., seals against) lip 232 when inflated. For some applications, inflation of the balloon obstructs 80-90 percent or 90-99 percent of opening 230. In contrast, in the deflated state of balloon 220, opening 230 is typically at least 50 percent (e.g., 60-90 percent) unobstructed by the balloon and/or shaft 216. The obstruction of opening 230 caused by inflation of balloon 220 reduces the risk of lip 232 engaging implant 20 during withdrawal. Because this functionality is provided by a balloon, when the balloon is deflated, cavity 242 is available to house at least part of implant 20.

Figure 3:
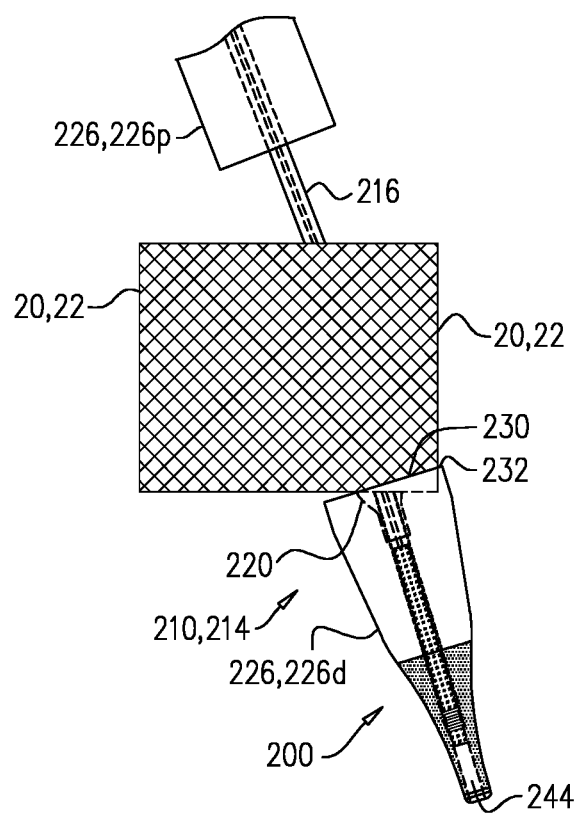
Figure 6A:
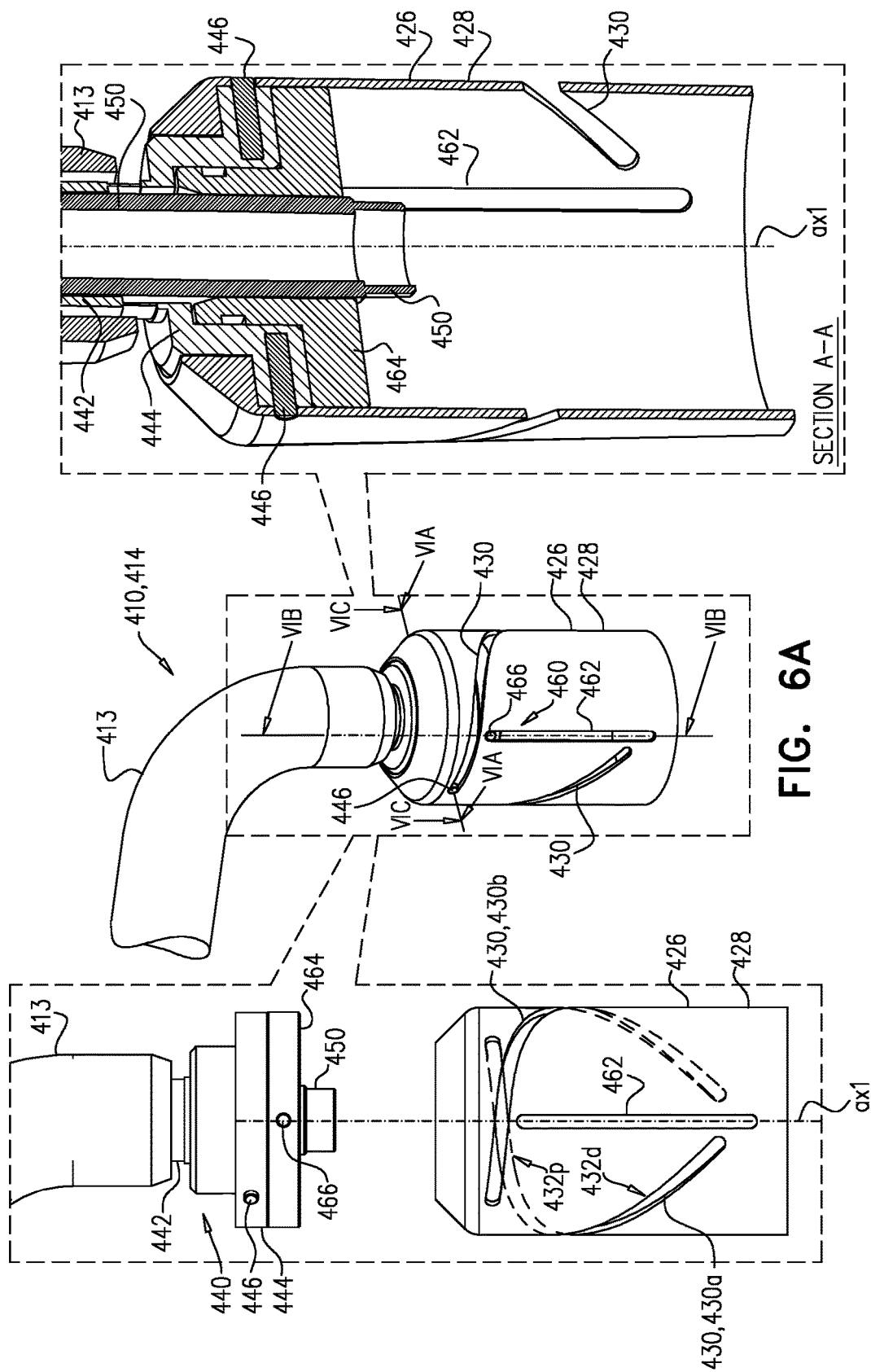

FIG. 2F shows distal part 214 of tool 210 being withdrawn via the lumen of implant 20, while balloon 220 (e.g., tapered portion 224 thereof) slides past parts of the implant that lip 232 may otherwise have engaged. FIG. 3 illustrates what may occur during withdrawal if balloon 220 is not inflated (or what may occur in a similar system that does not comprise balloon 220), and therefore demonstrates an advantage of system 200. In FIG. 3, lip 232 engages part of implant 20 (e.g., part of the implant enters cavity 242 via opening 230), impeding withdrawal of distal piece 226*d* and/or causing dislodgement of implant 20.

Reference is made to FIGS. 4A-D, which are schematic illustrations of a system 300, which comprises implant 20, and a tool 310 configured for transluminal delivery of the implant. Tool 310 comprises a shaft 316 that extends longitudinally from a proximal part 312 of the tool (which typically comprises a handle and/or controller), and has an open distal end 330. Implant 20 is reversibly coupled to the tool, and is disposed around a distal portion of shaft 316. Tool 310 comprises a sheath 326 that houses implant 20, and has a diameter that is dimensioned for transluminal delivery. Tool 310 further comprises a control element 334, disposed within shaft 316. Movement of control element 334 within shaft 316 is controllable by proximal part 312 of tool 310, and control element 334 is coupled to sheath 326 such that movement of the control element proximally within the shaft draws the sheath (i) distally off of implant 20, and (ii) into open distal end 330 of the shaft.

Typically, sheath 326 comprises a flexible sheet 328, such as a sheet or fabric of a polymer (e.g., nylon, polytetrafluoroethylene, polyester, or polyethylene terephthalate).

For some applications, sheet 328 defines sheath 326 as a single-walled sheath, and as it is drawn distally off of implant 20, it slides directly over implant 20 (e.g., is in contact with the implant).

For some applications, and as shown, sheet 328 is doubled-over itself to define an inner wall 329*a* of sheath 326 (i.e., defines the sheath as a double-walled sheath), and an outer wall 329*b* of the sheath (FIG. 4A). For such applications, a proximal opening 332 of sheath 326 is defined at a transition zone 336 between inner wall 329*a* and outer wall 329*b* (i.e., the zone at which sheet 328 transitions between defining the inner wall and defining the outer wall). That is, the transition zone defines a lip of the sheath, the lip defining proximal opening 332. The above-described movement of control element 334 proximally within shaft 316 draws (e.g., peels) sheath 326 distally off of implant 20 by drawing outer wall 329*b* progressively into open distal end 330 of the shaft such that progressively proximal regions of inner wall 329*a* transition through transition zone 336 to become part of the outer wall, and the transition zone (and thereby proximal opening 332 of the sheath) moves distally along the implant, exposing progressively distal regions of the implant (FIGS. 4B-C).

Inner wall 329*a* is typically in contact with implant 20 (e.g., constraining the implant to its compressed diameter), but outer wall 329*b* is not in contact with the implant. During the unsheathing of implant 20, neither inner wall 329*a* nor outer wall 329*b* slides directly over the implant while in contact with the implant. Rather, outer wall 329*b* slides over inner wall 329*a* (e.g., while in contact with the inner wall), and the sheath effectively peels off of the implant, thereby advantageously reducing friction that might be caused by direct sliding of the sheath over the implant while in contact with the implant.

FIG. 4D shows sheath 326 having been completely drawn off of implant 20, and the implant having responsively expanded.

Reference is now made to FIG. 5, which is a schematic illustration of a system 300*a*, which is an embodiment of system 300, in accordance with some applications of the invention. Elements in FIG. 5 that have a reference numeral suffixed "a" are equivalent, mutatis mutandis, to elements in FIGS. 4A-D that have the same reference numeral (without the suffix), except where noted. FIG. 5 shows the state of system 300*a* that is equivalent to the state of system 300 shown in FIG. 4B, mutatis mutandis.

As described for system 300, movement of control element 334*a* within shaft 316*a* is controllable by a proximal part of tool 310*a*, and control element 334*a* is coupled to sheath 326*a* such that movement of the control element proximally within the shaft draws the sheath (i) distally off of implant 20, and (ii) into open distal end 330*a* of the shaft. In system 300*a*, this movement of control element 334*a* is achieved by rotating the control element within shaft 316*a*. Shaft 316*a* and control element 334*a* define, respectively, complementary inner screw thread 342 and outer screw thread 344. FIG. 5 includes an enlarged inset view that shows shaft 316*a* as though it were opened up flat. Control element 334*a* comprises a shank 345, and a coupling 346, typically at a distal end of the control element, that is rotatably coupled to shank 345 (e.g., via a bearing 348). Coupling 346 is the portion of control element 334*a* that is coupled to sheath 326*a*. Due to mating of threads 342 and 344, rotation of shank 345 within shaft 316*a* causes control element 334*a* as a whole to move proximally within the shaft, while coupling 346 remains relatively rotationally stationary with respect to the shaft (e.g., coupling 346 slides longitudinally without rotating), thereby causing sheath 326*a* to be drawn (i) distally off of implant 20, and (ii) into open distal end 330*a* of the shaft, without the rotation of shank 345 twisting the sheath. That is, rotation of shank 345 within shaft 316*a* causes (i) screwing of the shank through the shaft, but (ii) sliding (e.g., linear sliding) of coupling 346 through the shaft.

For some applications, coupling 346 rotates slightly with respect to shaft 316*a*, but remains relatively rotationally stationary with respect to the shaft due to resistance provided by sheath 326*a*. For some applications, coupling 346 defines one or more fins 350 that each protrudes radially outward, and into a respective longitudinal groove 352 defined by shaft 316*a*. Fins 350 can slide only linearly along grooves 352, thereby inhibiting rotation of coupling 346 with respect to shaft 316*a*, but allowing the coupling to slide longitudinally along the shaft. For some applications, and as shown, grooves 352 and thread 342 may be defined on the same longitudinal region of shaft 316*a*, and may in fact transect each other.

Reference is made to FIGS. 6A-C and 7A-C, which are schematic illustrations of a tool 410, for use with an implant such as implant 20, in accordance with some applications of the invention. Typically, tool 410 is a delivery tool for transluminal delivery of implant 20. A system 400 may be provided, comprising implant 20 and tool 410.

Tool 410 comprises a housing (e.g., a sheath) 426 at a distal part 414 of the tool. Housing 426 comprises a tubular wall 428 that circumscribes a longitudinal axis ax1 of the distal part of tool 410. Housing 426 is dimensioned to house at least part of implant 20. Housing 426 (e.g., wall 428 thereof) defines a track 430 that follows a generally-helical path around longitudinal axis ax1. Tool 410 further comprises a controller 440 that comprises a rod 442 and an actuator 444. Rod 442 extends from a proximal part of the tool to housing 426. Actuator 444 is rotatable with respect to housing 426, and is typically fixedly coupled to rod 442. Actuator 444 comprises an engaging element 446 that engages track 430. Controller 440 and housing 426 mechanically cooperate such that rotation of actuator 444 with respect to the housing (e.g., by rotation of rod 442) slides the housing longitudinally with respect to the actuator.

Typically, this movement is bidirectional. That is, rotation of actuator 444 in a first direction with respect to housing 426 slides the housing proximally with respect to the actuator, and rotation of the actuator in a second, opposite direction with respect to the housing slides the housing distally with respect to the actuator.

Typically, and as shown, housing 426 is dimensioned to house implant 20 such that track 430 is disposed around at least the part of implant 420. That is, typically, at least part of implant 20 is coincident, along axis ax1, with at least part of track 430.

For some applications, housing 426 defines more than one track 430, rotationally-offset from each other e.g., in order to evenly distribute forces applied by actuator 444 (which for such applications typically comprises a corresponding more than one engaging element 446). For example, and as shown, housing 426 may define two tracks 430a and 430b, rotationally-offset by 180 degrees from each other, and actuator 444 may comprise a corresponding two engaging elements 446, also rotationally-offset by 180 degrees from each other. For the sake of clarity, reference numerals 430a and 430b are only used in FIG. 6A.

Figure 7A:
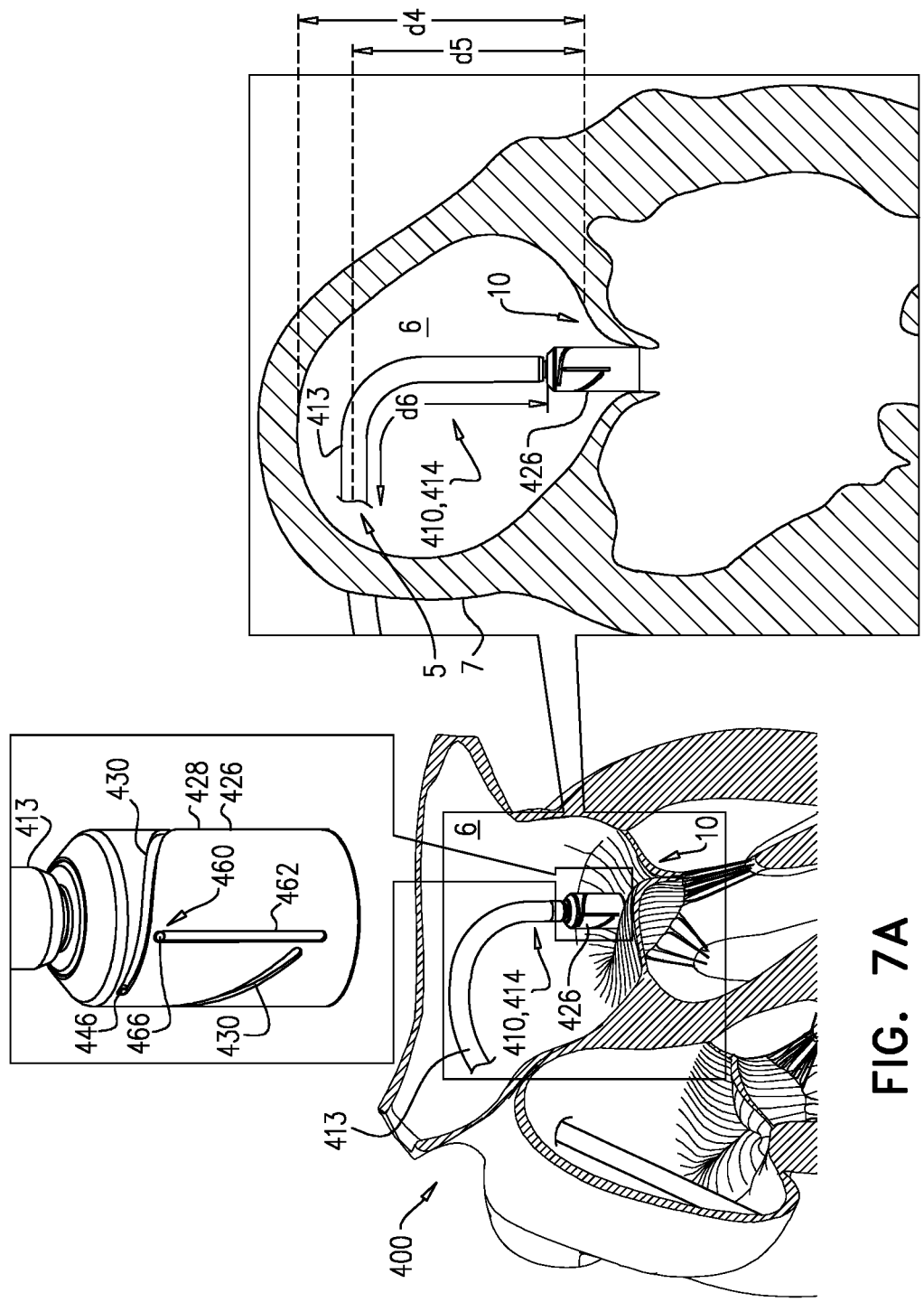
Figure 7B:
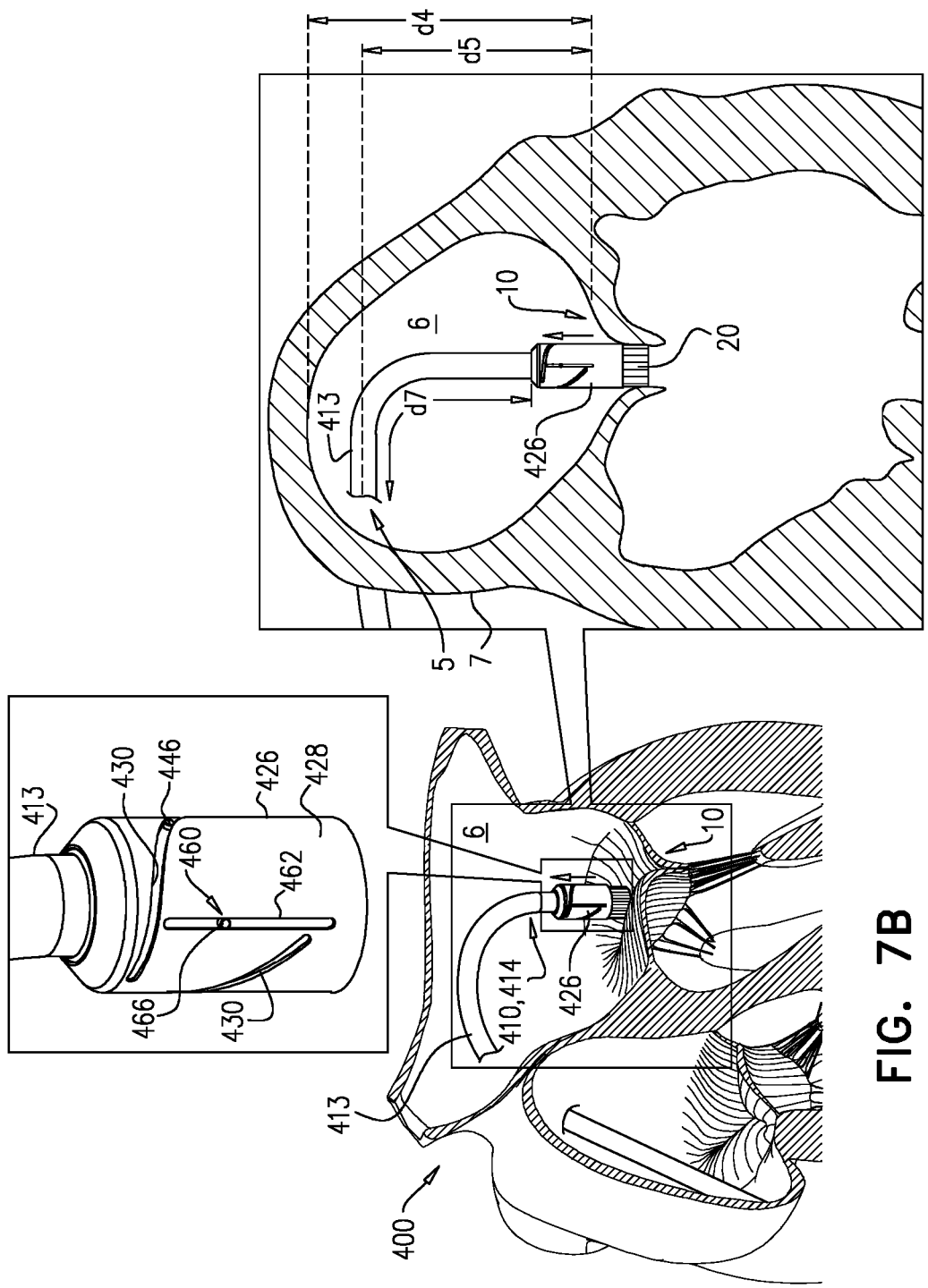
Figure 7C:
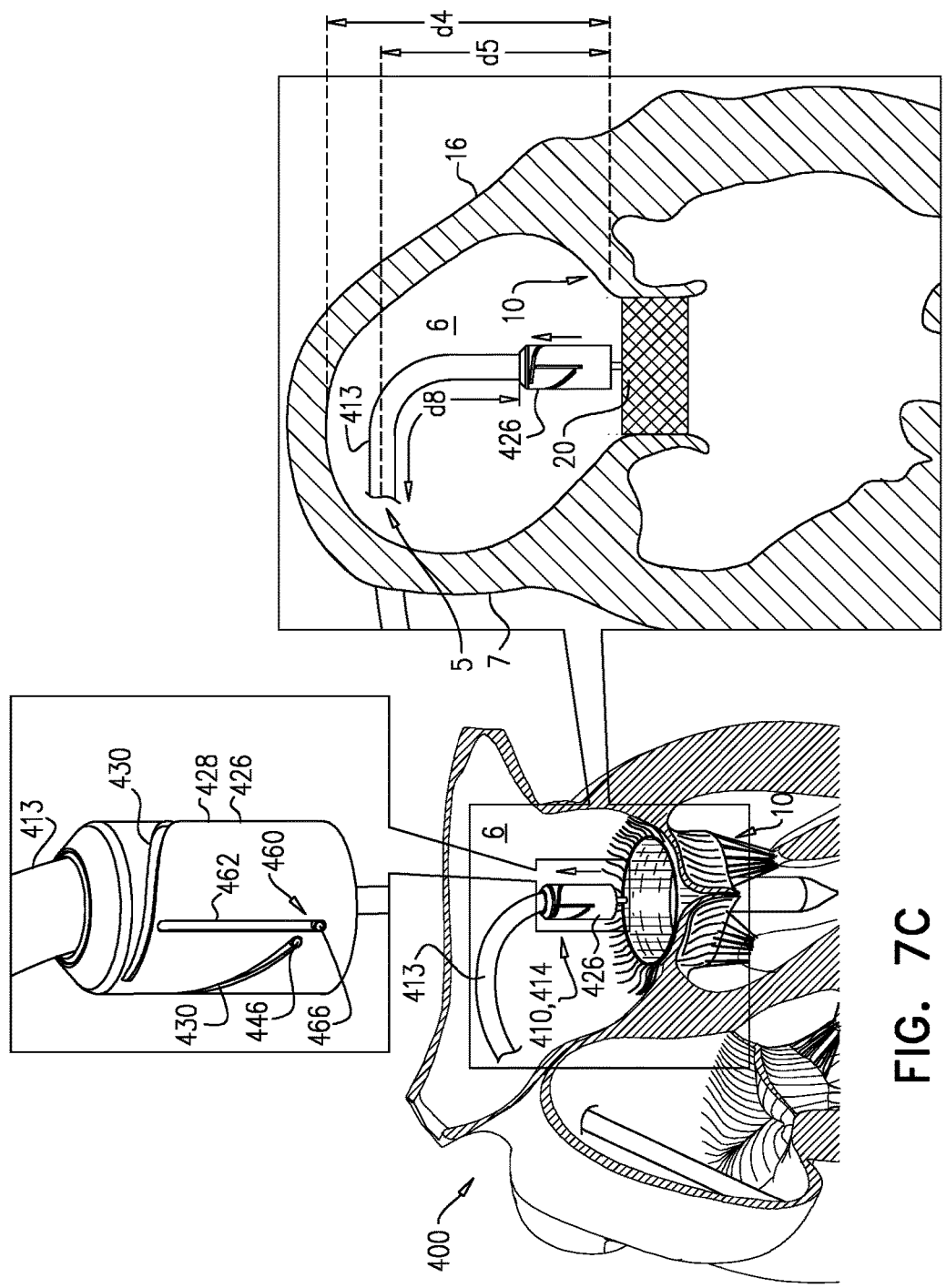

Typically, tool 410 further comprises a catheter 413 (e.g., a mid-portion of the tool), longitudinally disposed between the proximal part of the tool, such as a control handle, and distal part 414. Housing 426 is typically disposed distally to catheter 413. Rod 442 extends through catheter 413, and typically into housing 426. The mechanical cooperation between controller 440 and housing 426 is such that, to retract the housing from implant 20 (i.e., to deploy the part of the implant housed by the housing) rotation of actuator 444 with respect to the housing slides the housing proximally along and over part of the catheter. This is illustrated in FIGS. 7A-C, which show progressive steps in the retraction of housing 426 to deploy implant 20. Distances d6, d7, and d8 are each measured along catheter 413, between a given point on the catheter (e.g., a point of entry into atrium 6) and housing 426. Distance d7 is smaller than distance d6, and distance d8 is smaller than distance d7.

As described hereinabove, the dimensions of left atrium 6 limit maneuverability when implanting an implant at mitral valve 10 transseptally (e.g., transfemorally). For example, the height d4 of atrium 6, and/or the height d5 between the mitral valve and the entry point 5 of a delivery tool through septum 7 (e.g., the fossa ovalis), limit the distance to which the delivery tool can be raised away from the mitral valve in order to withdraw the housing or sheath of the tool from over the implant in order to deploy the implant. In particular, these heights limit the ability to raise the tool away from the mitral valve without moving and/or angling the tool toward entry point 5, and thereby tilting the implant with respect to the mitral valve. It is hypothesized by the inventors that tool 410 facilitates deployment of an implant at the mitral valve, and/or deployment without tilting the implant, because the retraction of housing 426 over catheter 413 replaces at least some of the otherwise required withdrawal of the delivery tool as a whole. For some applications, and as shown in FIGS. 7A-C, once catheter 413 and the implant within are in the correct position (FIG. 7A) deployment of the implant is possible without further movement of catheter 413 (FIGS. 7B-C).

Tool 410 typically further comprises a shaft 450 to which implant 20 is fixable, the shaft being slidably coupled housing 426, and extending proximally from the housing. Shaft 450 thereby serves as a mount for implant 20, and facilitates movement of other parts of tool 410 (e.g., housing 426) with respect to the implant.

Typically, tool 410 is configured in a manner that inhibits housing 426 from rotating in response to rotation of actuator 444, because the differential rotation causes the retraction of the housing. Therefore, tool 410 therefore typically comprises a housing-rotation inhibitor 460. For some applications, and as shown, housing-rotation inhibitor 460 comprises (i) a second track 462 that follows a generally-linear path parallel to longitudinal axis ax1, and (ii) a second engaging element 466. Engaging element 466 is fixedly coupled to shaft 450 (e.g., via a mount 464), and engages track 462, thereby rotationally fixing the shaft with respect to housing 426, while facilitating longitudinal sliding of the shaft with respect to the housing. Therefore, controller 440 and housing 426 mechanically cooperate such that rotation of actuator 444 with respect to the housing slides the track 462 longitudinally with respect to engaging element 466.

For some applications, housing 426 defines more than one second track 462, rotationally-offset from each other, e.g., in order to evenly distribute forces applied to it by, for example, a corresponding more than one engaging element 466. For example, and as shown, housing 426 may define two tracks 462, rotationally-offset by 180 degrees from each other, and tool 410 may comprise a corresponding two engaging elements 466, also rotationally-offset by 180 degrees from each other.

Typically, rod 442 is coaxial with shaft 450. Further typically, shaft 450 is disposed within rod 442 (which is typically disposed within catheter 413). Typically, actuator 444 defines a hole therethrough, through which shaft 450 extends. For example, at least part of shaft 450 may be disposed within housing 426, and the shaft extends distally out of catheter 413, through the hole in actuator 444, and into the housing.

The term "generally helical" is used with respect to the path of track 430 because the path may not be a true helix. For example, for some applications, and as shown, the pitch of the generally-helical path of the track differs along its length. For some such applications, a first portion 432p of the generally-helical path has a first pitch, and a second portion 432d of the generally-helical path, which is distal to the first portion, has a second pitch that is greater than the first pitch. For example, the pitch of the generally-helical path may gradually increase, such that it is progressively greater at progressively distal portions of the generally-helical path. It is hypothesized by the inventors that this facilitates (i) application of greater linear force during the initial stage of deployment from housing 426, while more of implant 20 is disposed in the housing and friction between the implant and housing is greater, and (ii) greater linear movement during later stages of deployment from housing 426, after some of the implant has already exited the housing, and friction between the implant and housing has been reduced. Alternatively or additionally, the distance of track 430 from longitudinal axis ax1 may differ along its length. For example, housing 426 may be wider toward its distal opening, and track 430, defined by the housing, may correspondingly become increasingly further from axis ax1 toward the distal opening of the housing.

Figure 8:
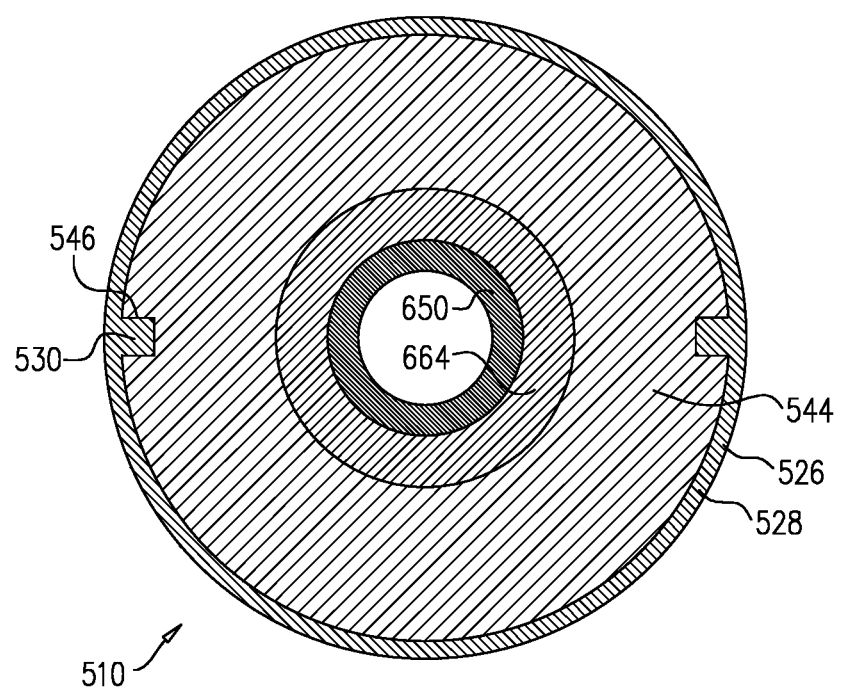
FIG. 8 is a schematic illustration of an alternative tool, in accordance with some applications of the invention.

Typically, and as shown, track 432 is a channel (e.g., cut into housing 426, such as into tubular wall 428 thereof), and engaging element 446 is a spur that engages the track by protruding into the channel. However, alternative tracks and engaging elements may be used. For example, and as shown in FIG. 8, to which reference is now additionally made, the track may be a rail, and the engaging element may be a notch that engages the track by receiving the rail. FIG. 8 is a schematic illustration of alternative tool 510, in accordance with some applications of the invention. Except where noted, tool 510 is identical to tool 410, and its components are identical to identically-named components of tool 410. FIG. 8 shows a transverse cross-section of tool 510 that substantially corresponds to the transverse cross-section of tool 410 that is shown in FIG. 6C. As shown, a track 530 (which substantially corresponds to track 430 of tool 410) is a rail that protrudes radially-inward from a tubular wall 528 of a housing 526, and an engaging element 546 is a notch defined by an actuator 544, the notch receiving the rail.

Second track 462 and second engaging element 466 are shown as a channel and spur, but may, alternatively or additionally, be similarly substituted with a rail and notch, mutatis mutandis. For example, tool 510 may comprise a shaft 550 to which is fixedly coupled an engaging element (not shown in FIG. 8), e.g., via a mount 564.

For some applications, the first track and the first engaging element are of the channel-and-spur type, and the second track and the second engaging element are of the rail-and-notch type. For some applications, the first track and the first engaging element are of the rail-and-notch type, and the second track and the second engaging element are of the channel-and-spur type. For some applications, both are of the channel-and-spur type (e.g., as shown for tool 410). For some applications, both are of the rail-and-notch type.

Reference is again made to FIGS. 1A-8. The components of the systems described herein may be combined in various ways. For example, balloon 120 may be used (in addition to or in place of the above-described components) in system 200 and/or in system 300, mutatis mutandis; balloon 220 may be used (in addition to or in place of the above-described components) in system 100 and/or in system 300, mutatis mutandis; and/or sheath 326 may be used (in addition to or in place of the above-described components) in system 100 or in system 200, mutatis mutandis.

Similarly, tool 410, or elements thereof, may be used in combination with other embodiments described herein. For example, housing 426 may serve as a proximal piece of a sheath (e.g., sheath 226) that also has a distal piece, housing 426 being moved proximally to deploy a proximal part of the housed implant, and the distal piece of the sheath being moved distally to deploy a distal part of the housed implant. That is, for some applications, housing 426 is a proximal housing that is dimensioned to house a first part of the implant, and has a distal opening for deployment of the first part of the implant therethrough; and the tool further comprises a distal housing that is dimensioned to house a second part of the implant, and has a proximal opening, facing the distal opening, for deployment of the second part of the implant therethrough. For such applications, both housings are typically independently slidable with respect to the implant, and also with respect to shaft 450.

The term "diameter," which is used throughout this application (including the specification and the claims), refers to a dimension of the component that is transverse to the longitudinal axis of the component and/or of the system as a whole. The term "diameter" is used because such components typically have a circular transverse cross-section. However, it is to be understood that the descriptions may equally apply to equivalent components that have a non-circular cross-section, mutatis mutandis.

Each of the systems described hereinabove is described as comprising implant 20. However, it is to be noted that the scope of the invention includes systems that do not comprise an implant—i.e., systems that are otherwise the same as those described, but which are provided as delivery systems for an implant that is not included.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    an implant:
        comprising (i) a frame that defines a central longitudinal lumen, and (ii) prosthetic valve leaflets disposed within the lumen,
        constrainable, by a constraining force, in a compressed state in which the lumen has a compressed internal diameter,
        having an expanded state into which the implant automatically transitions upon removal of the constraining force, and in which the lumen has an expanded internal diameter; and
    a tool, configured for transluminal delivery of the implant, the tool comprising:
        a shaft that extends longitudinally from a proximal part of the tool;
        a nosepiece fixed to the shaft, and arranged with respect to the implant such that the implant extends proximally away from the nosepiece and over the shaft; and
        a balloon, in fluid communication with the proximal part of the tool,
    wherein:
        the balloon has:
            a maximally-inflated state in which the balloon (i) has a widest part that has an inflated external diameter that is smaller than the expanded internal diameter, (ii) has a tapered portion that tapers longitudinally away from the widest part and from the nosepiece, and (iii) is dimensioned such that, while the implant is in its expanded state, the balloon is withdrawable by sliding of the balloon through the lumen, between the leaflets, and out of the lumen, and
            a deflated state in which the widest part has a deflated external diameter that is smaller than the inflated external diameter, and
        the apparatus has a delivery state in which:
            the implant is in the compressed state,
            the balloon is in the deflated state, and
            a portion of the balloon is disposed within the lumen.

2. The apparatus according to claim 1, wherein the nosepiece is fixed to the distal end of the shaft.

3. The apparatus according to claim 1, wherein the tapered portion tapers proximally away from the widest part and from the nosepiece.

4. The apparatus according to claim 1, wherein:
the nosepiece is arranged with respect to the implant such that the implant extends proximally over the shaft with the shaft within the lumen of the implant,
the implant assumes the expanded state upon implantation of the implant, and
the nosepiece is dimensioned to be withdrawable proximally through the lumen while the implant is in its expanded state.

5. The apparatus according to claim 4, wherein the nosepiece is not dimensioned to be withdrawable proximally through the lumen while the implant is in its compressed state.

6. The apparatus according to claim 1, wherein:
the tool further comprises a sheath that has a diameter that is dimensioned for transluminal delivery, and
in the delivery state, the sheath houses the implant.

7. Apparatus, comprising:
an implant:
    comprising (i) a frame that defines a central longitudinal lumen, and (ii) prosthetic valve leaflets disposed within the lumen,
    constrainable, by a constraining force, in a compressed state in which the lumen has a compressed internal diameter,
    having an expanded state into which the implant automatically transitions upon removal of the constraining force, and in which the lumen has an expanded internal diameter; and
a tool, configured for transluminal delivery of the implant, the tool comprising:
    a shaft that extends longitudinally from a proximal part of the tool;
    a nosepiece fixed to the shaft, and arranged with respect to the implant such that the implant extends proximally away from the nosepiece and over the shaft; and
    a balloon, in fluid communication with the proximal part of the tool,
wherein:
    the balloon has:
        a maximally-inflated state in which the balloon (i) has a widest part that has an inflated external diameter that is less than 90 percent of the expanded internal diameter, and (ii) has a tapered portion that tapers longitudinally away from the widest part and from the nosepiece, and
        a deflated state in which the widest part has a deflated external diameter that is smaller than the inflated external diameter, and
    the apparatus has a delivery state in which:
        the implant is in the compressed state,
        the balloon is in the deflated state, and
        a portion of the balloon is disposed within the lumen.

8. The apparatus according to claim 7, wherein the nosepiece is fixed to the distal end of the shaft.

9. The apparatus according to claim 7, wherein the tapered portion tapers proximally away from the widest part and from the nosepiece.

10. The apparatus according to claim 7, wherein:
the nosepiece is arranged with respect to the implant such that the implant extends proximally over the shaft with the shaft within the lumen of the implant,
the implant assumes the expanded state upon implantation of the implant, and
the nosepiece is dimensioned to be withdrawable proximally through the lumen while the implant is in its expanded state.

11. The apparatus according to claim 10, wherein the nosepiece is not dimensioned to be withdrawable proximally through the lumen while the implant is in its compressed state.

12. The apparatus according to claim 7, wherein:
the tool further comprises a sheath that has a diameter that is dimensioned for transluminal delivery, and
in the delivery state, the sheath houses the implant.

13. Apparatus, comprising:
an implant:
    comprising (i) a frame that defines a central longitudinal lumen, and (ii) a valve member disposed within the lumen,
    constrainable, by a constraining force, in a compressed state in which the lumen has a compressed internal diameter,
    having an expanded state into which the implant automatically transitions upon removal of the constraining force, and in which the lumen has an expanded internal diameter; and
a tool, configured for transluminal delivery of the implant, the tool comprising:
    a shaft that extends longitudinally from a proximal part of the tool;
    a nosepiece fixed to the shaft, and arranged with respect to the implant such that the implant extends proximally away from the nosepiece and over the shaft; and
    a balloon, in fluid communication with the proximal part of the tool,
wherein:
    the balloon has:
        a maximally-inflated state in which the balloon (i) has a widest part that has an inflated external diameter that is smaller than the expanded internal diameter and can fit through the valve member, (ii) has a tapered portion that tapers longitudinally away from the widest part and from the nosepiece, and
        a deflated state in which the widest part has a deflated external diameter that is smaller than the inflated external diameter, and
    the apparatus has a delivery state in which:
        the implant is in the compressed state,
        the balloon is in the deflated state, and
        a portion of the balloon is disposed within the lumen.

14. The apparatus according to claim 13, wherein the nosepiece is fixed to the distal end of the shaft.

15. The apparatus according to claim 13, wherein the tapered portion tapers proximally away from the widest part and from the nosepiece.

16. The apparatus according to claim 13, wherein:
the nosepiece is arranged with respect to the implant such that the implant extends proximally over the shaft with the shaft within the lumen of the implant,
the implant assumes the expanded state upon implantation of the implant, and
the nosepiece is dimensioned to be withdrawable proximally through the lumen while the implant is in its expanded state.

17. The apparatus according to claim 16, wherein the nosepiece is not dimensioned to be withdrawable proximally through the lumen while the implant is in its compressed state.

18. The apparatus according to claim 13, wherein:
the tool further comprises a sheath that has a diameter that is dimensioned for transluminal delivery, and
in the delivery state, the sheath houses the implant.

* * * * *